US012597509B2

(12) United States Patent
Boulos et al.

(10) Patent No.: US 12,597,509 B2
(45) Date of Patent: Apr. 7, 2026

(54) SYSTEMS AND METHODS FOR MEDICAL DEVICE TASK GENERATION AND MANAGEMENT

(71) Applicant: Sage Products, LLC, Cary, IL (US)

(72) Inventors: Catherine Boulos, Vernon Hills, IL (US); Ronald Cagle, Crystal Lake, IL (US); Heather Mercier, Rockford, IL (US); Theresa Sebastian, Chicago, IL (US)

(73) Assignee: Sage Products, LLC, Cary, IL (US)

( * ) Notice: Subject to any disclaimer, the term of this patent is extended or adjusted under 35 U.S.C. 154(b) by 269 days.

(21) Appl. No.: 17/559,797

(22) Filed: Dec. 22, 2021

(65) Prior Publication Data

US 2022/0199240 A1 Jun. 23, 2022

Related U.S. Application Data

(60) Provisional application No. 63/130,096, filed on Dec. 23, 2020.

(51) Int. Cl.
*G16H 40/20* (2018.01)
*G06K 7/10* (2006.01)
(Continued)

(52) U.S. Cl.
CPC ......... *G16H 40/20* (2018.01); *G06K 7/10366* (2013.01); *G06K 7/1413* (2013.01);
(Continued)

(58) Field of Classification Search
CPC ......... G16H 40/20; G16H 10/60; G16H 40/67
See application file for complete search history.

(56) References Cited

U.S. PATENT DOCUMENTS

| | | | | |
|---|---|---|---|---|
| 9,582,838 B1 * | 2/2017 | Henderson | ............. | G16H 40/63 |
| 2002/0096180 A1 * | 7/2002 | Teller | .................... | A61B 90/00 |
| | | | | 128/897 |

(Continued)

FOREIGN PATENT DOCUMENTS

WO    WO-2018093706 A1 *   5/2018    ......... G06K 7/10316

OTHER PUBLICATIONS

International Search Report and Written Opinion for International Application No. PCT/US2021/064948, mailed Apr. 7, 2022, 15 pages.

*Primary Examiner* — Evangeline Barr
(74) *Attorney, Agent, or Firm* — Foley & Lardner LLP

(57) ABSTRACT

A method for generating and managing one or more tasks associated with a medical device includes receiving, by a medical device task generation and management system, patient data associated with a patient, receiving, by the system, device data associated with the medical device, and generating, by the system, one or more tasks based on the device data, each task of the one or more tasks including a due date, a due time, and task data. The method further includes providing, by the medical device task generation and management system, an indicator for each of the one or more tasks, the indicator providing an indication of a completion status of each task based on the due date and due time of the task, and determining, by the medical device task generation and management system, that at least one of the one or more tasks has been completed.

23 Claims, 15 Drawing Sheets

(51) Int. Cl.
    *G06K 7/14*         (2006.01)
    *G16H 10/60*      (2018.01)
    *G16H 40/67*      (2018.01)

(52) U.S. Cl.
    CPC ........... *G06K 7/1417* (2013.01); *G16H 10/60*
                (2018.01); *G16H 40/67* (2018.01)

(56)              References Cited

U.S. PATENT DOCUMENTS

| | | | |
|---|---|---|---|
| 2005/0258956 A1* | 11/2005 | Neuwirth | G06Q 10/087 |
| | | | 340/8.1 |
| 2009/0012822 A1 | 1/2009 | Ross et al. | |
| 2009/0182594 A1* | 7/2009 | Choubey | G06Q 10/06 |
| | | | 705/7.33 |
| 2009/0313046 A1 | 12/2009 | Badgett et al. | |
| 2011/0178818 A1 | 7/2011 | Jonsson | |
| 2013/0204145 A1* | 8/2013 | Shah | A61B 5/0205 |
| | | | 709/201 |
| 2015/0242585 A1* | 8/2015 | Spiegel | G16H 10/60 |
| | | | 705/2 |
| 2015/0371176 A1* | 12/2015 | Barrett | G06Q 10/0631 |
| | | | 705/2 |
| 2016/0300178 A1* | 10/2016 | Perry | G06Q 10/063112 |
| 2019/0392929 A1* | 12/2019 | Gassman | G16H 10/60 |

\* cited by examiner

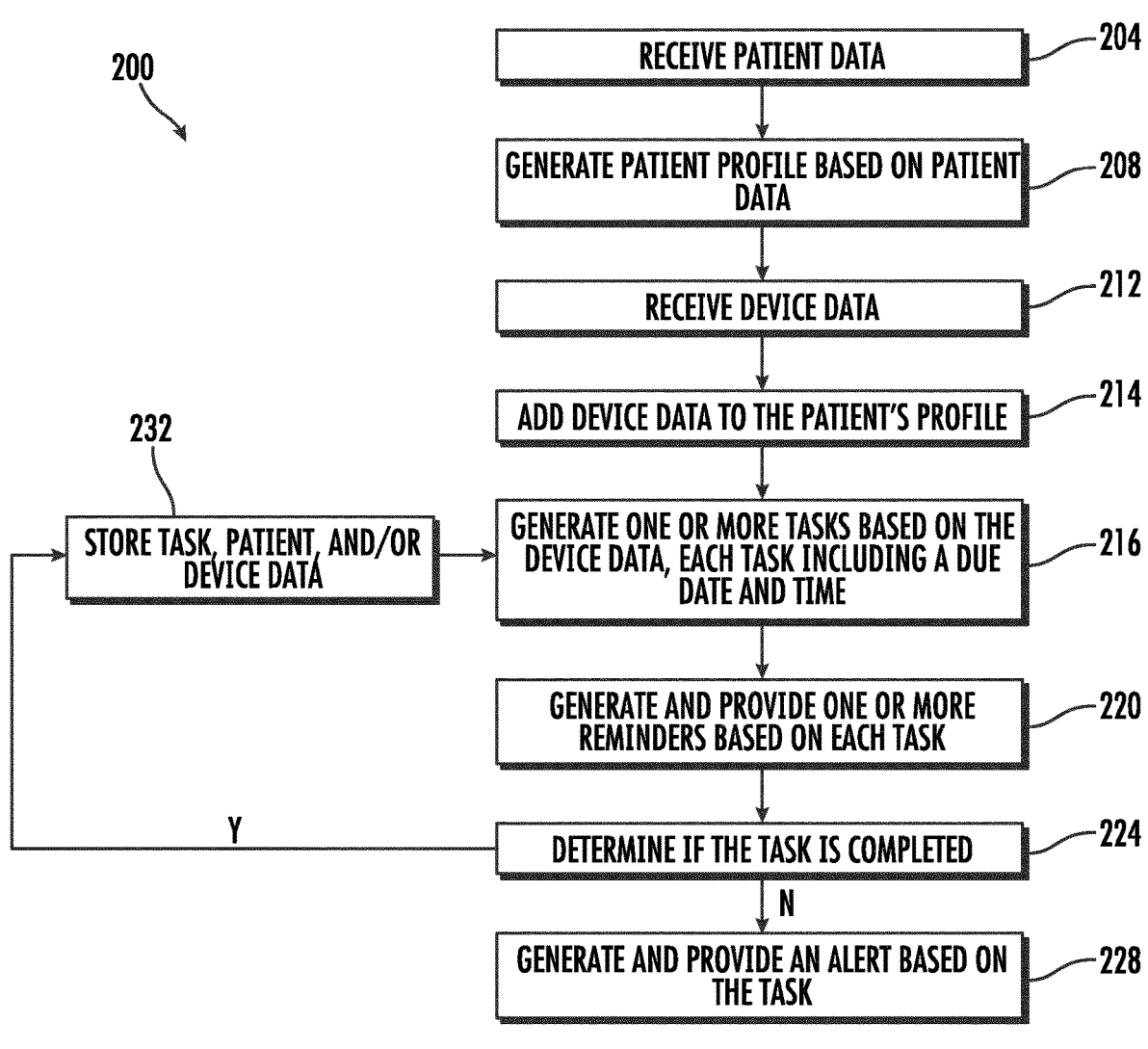

200

204 — RECEIVE PATIENT DATA

208 — GENERATE PATIENT PROFILE BASED ON PATIENT DATA

212 — RECEIVE DEVICE DATA

214 — ADD DEVICE DATA TO THE PATIENT'S PROFILE

232 — STORE TASK, PATIENT, AND/OR DEVICE DATA

216 — GENERATE ONE OR MORE TASKS BASED ON THE DEVICE DATA, EACH TASK INCLUDING A DUE DATE AND TIME

220 — GENERATE AND PROVIDE ONE OR MORE REMINDERS BASED ON EACH TASK

Y

224 — DETERMINE IF THE TASK IS COMPLETED

N

228 — GENERATE AND PROVIDE AN ALERT BASED ON THE TASK

FIG. 3

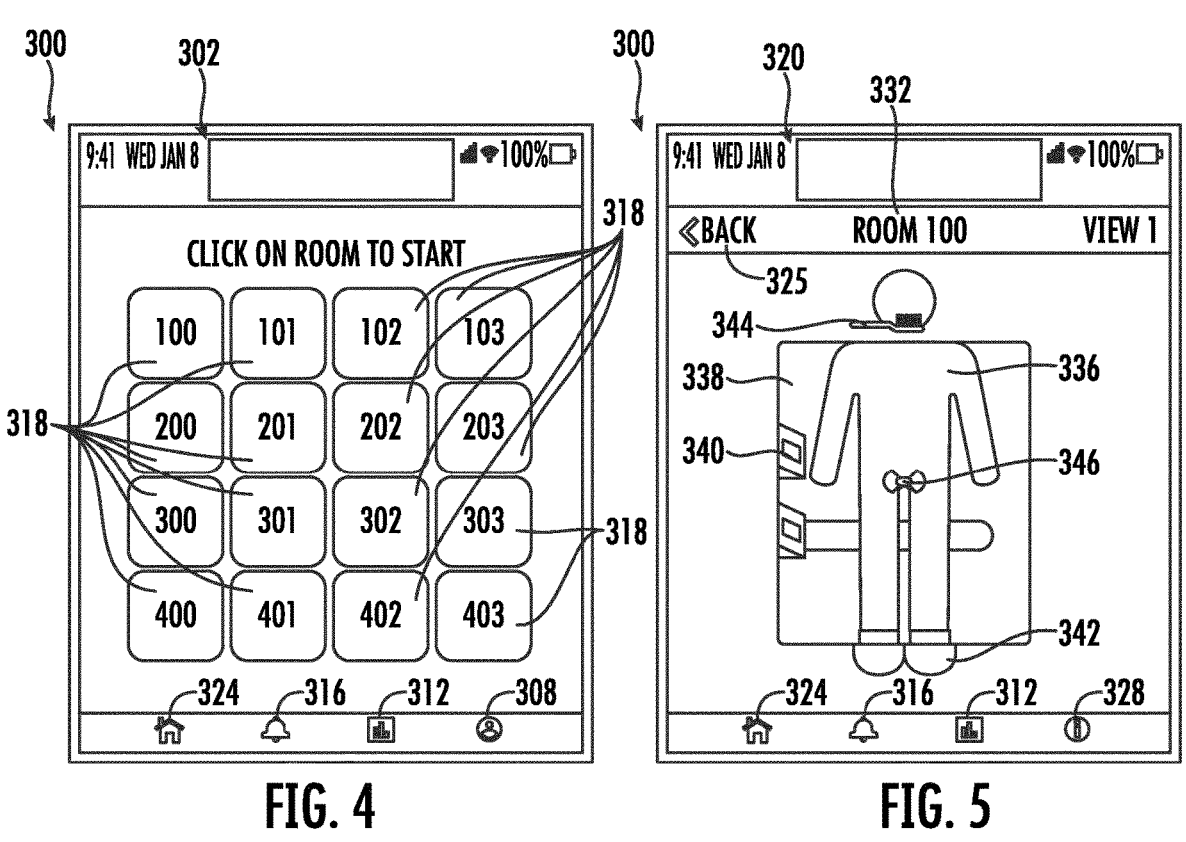
FIG. 4
FIG. 5
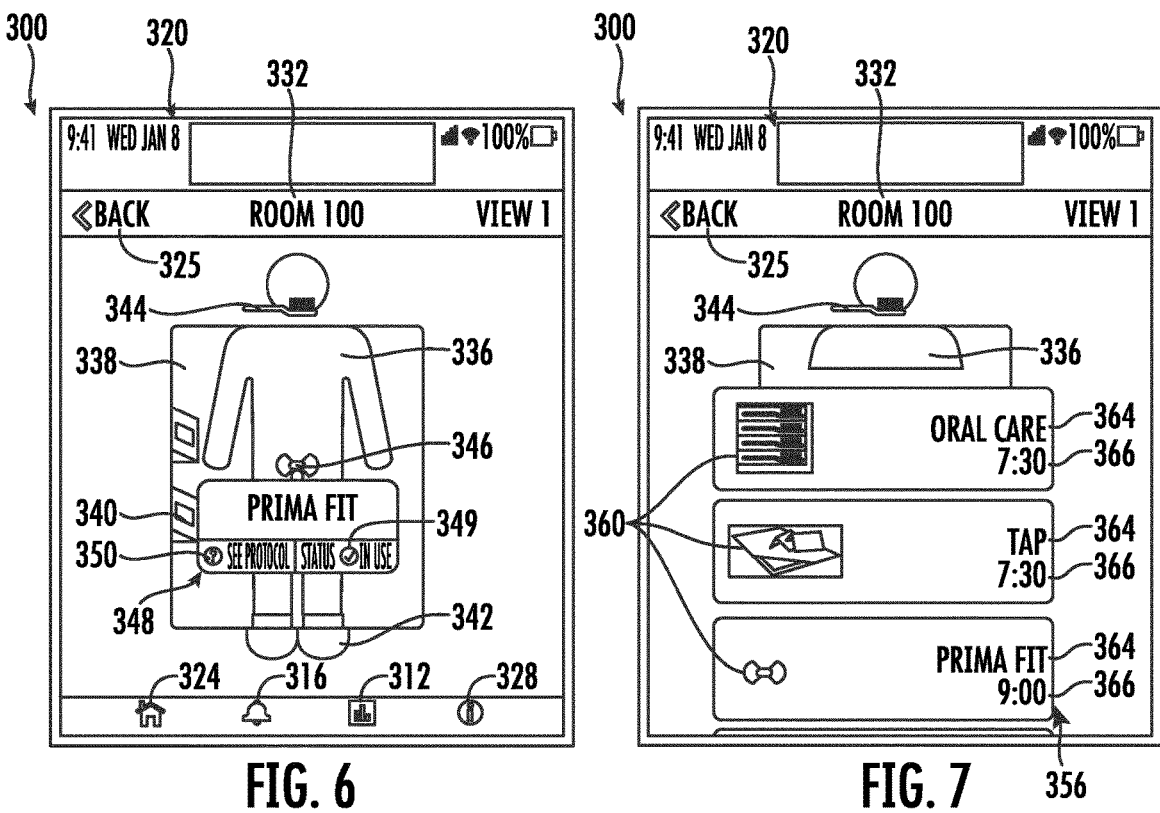
FIG. 6
FIG. 7

300    368

370

325

500

RECEIVE AT LEAST ONE OF PATIENT DATA, DEVICE DATA, AND TASK DATA — 504

RECEIVE A REQUEST TO GENERATE A CUSTOM REPORT, THE REQUEST INCLUDING ONE OR MORE INPUTS — 508

GENERATE THE CUSTOM REPORT BASED ON THE REQUEST AND THE ONE OR MORE INPUTS OF THE REQUEST — 512

PROVIDE THE CUSTOM REPORT — 516

600

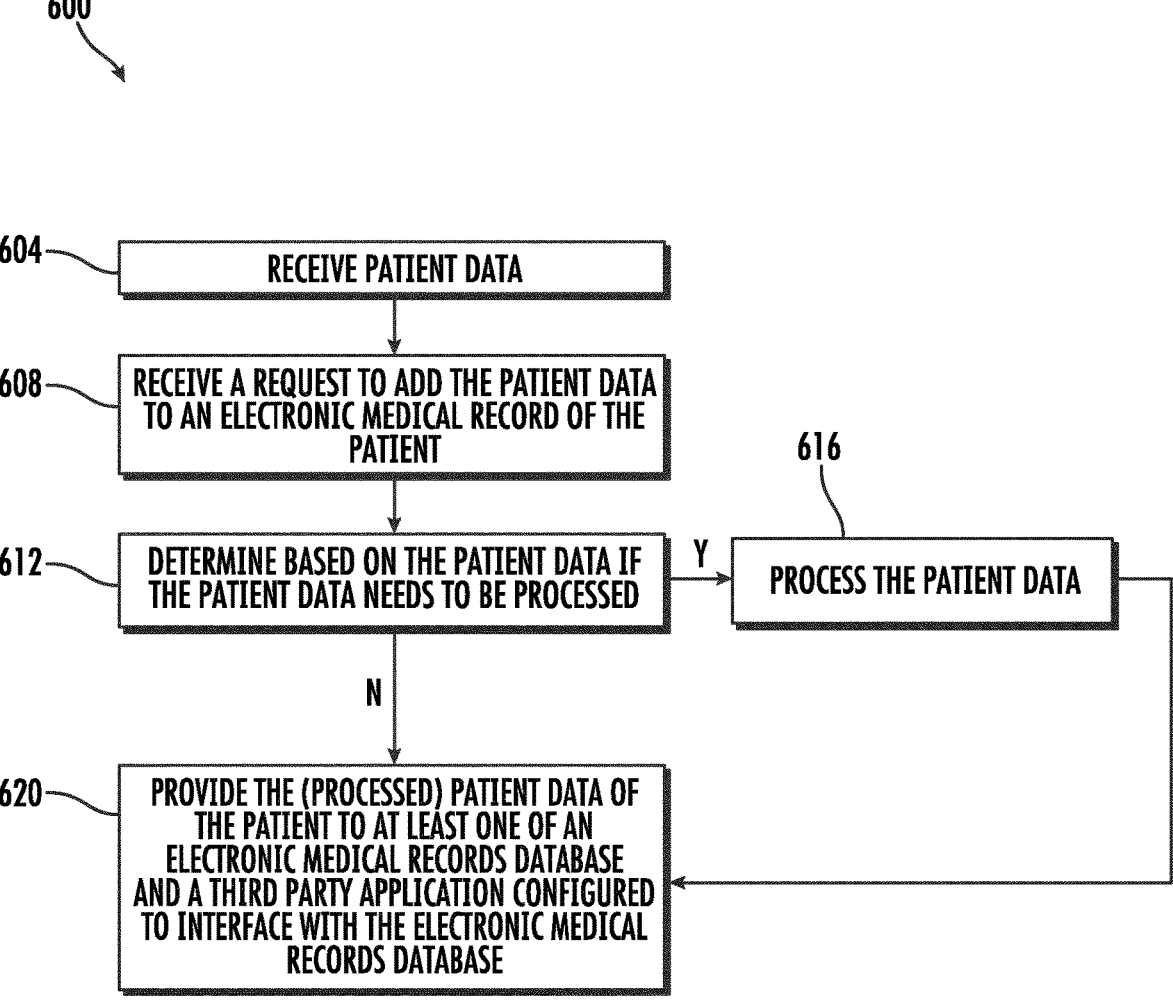

604 — RECEIVE PATIENT DATA

608 — RECEIVE A REQUEST TO ADD THE PATIENT DATA TO AN ELECTRONIC MEDICAL RECORD OF THE PATIENT

616

612 — DETERMINE BASED ON THE PATIENT DATA IF THE PATIENT DATA NEEDS TO BE PROCESSED

Y    PROCESS THE PATIENT DATA

N

620 — PROVIDE THE (PROCESSED) PATIENT DATA OF THE PATIENT TO AT LEAST ONE OF AN ELECTRONIC MEDICAL RECORDS DATABASE AND A THIRD PARTY APPLICATION CONFIGURED TO INTERFACE WITH THE ELECTRONIC MEDICAL RECORDS DATABASE

FIG. 25

SYSTEMS AND METHODS FOR MEDICAL DEVICE TASK GENERATION AND MANAGEMENT

CROSS-REFERENCE TO RELATED APPLICATIONS

This claims the benefit of U.S. Provisional Patent Application No. 63/130,096, filed Dec. 23, 2020, which is incorporated herein by reference in its entirety.

BACKGROUND

The present disclosure relates to systems and methods for workflow management within the field of healthcare. More specifically, the present disclosure relates to workflow management relating to medical devices and the tasks that the medical devices generate.

The present disclosure provides a system and method for improving workflow and compliance of medical personnel relating to tracking and use of disposable devices during patient care.

SUMMARY

The following presents a general summary of aspects of the invention in order to provide a basic understanding of the invention. This summary is not an extensive overview of the invention. It is not intended to identify key or critical elements of the invention or to delineate the scope of the invention. The following summary merely presents some concepts of the invention in a general form as a prelude to the more detailed description provided below.

One aspect of the present disclosure relates to a computer-implemented method for generating and managing one or more tasks associated with a medical device. The method includes receiving, by a medical device task generation and management system, patient data associated with a patient, receiving, by the medical device task generation and management system, device data associated with the medical device, and generating, by the medical device task generation and management system, one or more tasks based on the device data, each task of the one or more tasks including a due date, a due time, and task data. The method further includes providing, by the medical device task generation and management system, an indicator for each of the one or more tasks, the indicator providing an indication of a completion status of each task based on the due date and due time of the task, and determining, by the medical device task generation and management system, that at least one of the one or more tasks has been completed.

In various embodiments, the device data is received using at least one of an RFID reader, a quick response (QR) code scanner, and a barcode scanner. In some embodiments, the method also includes storing, by the medical device task generation and management system, the task data associated with the at least one of the one or more tasks that has been completed in a server database. In other embodiments, the patient data includes at least one of a room number, a name, and a date of birth of the patient. In yet other embodiments, providing the indicator further includes displaying, by a computing device, a user interface including a patient representation, generating and disposing, by the computing device, a device representation based on the device data on the patient representation, and updating, by the computing device, a color of the device representation based on the due date and the due time. In various embodiments, the color of the device representation is updated to be at least one of green, yellow, and red.

In some embodiments, the method also includes receiving, by the medical device task generation and management system, a request to update an electronic medical record of the patient, and providing, by the medical device task generation and management system, at least one of the patient data, the task data, and the device data to a third party electronic health record application. In other embodiments, at least one of the patient data, the task data, and the device data is provided via an application programming interface of the third party electronic health record application. In yet other embodiments, determining that at least one of the one or more tasks has been completed includes receiving, by the medical device task generation and management system, an indication that at least one of the one or more tasks has been completed from a staff computing device. In various embodiments, the medical device includes a first medical device and determining that at least one of the one or more tasks has been completed includes receiving, by the medical device task generation and management system, device data associated with a second medical device, where the second medical device and the first medical device are the same device type. In some embodiments, generating the one or more tasks includes providing, by a staff computing device, the task data associated with the medical device to at least one of a server computing device of the medical device task generation and management system and a health care provider computing device of the medical device task generation and management system, searching, by the at least one of the server computing device and the health care provider computing device, a device database for the one or more tasks associated with the device data, and in response to the device database having the one or more tasks associated with the device data, providing, by the at least one of the server computing device and the health care provider computing device, the one or more tasks associated with the device data to the staff computing device.

Another aspect of the present disclosure relates to a medical device task generation and management system. The system includes a staff computing device that has a network interface and a processing circuit, where the network interface is structured to facilitate data communication with a server computing device via a network, and the processing circuit has a processor and a memory. The processing circuit is structured receive patient data associated with a patient, receive device data associated with a medical device, and identify one or more tasks based on at least one of the device data or the patient data, where each task one of the one or more tasks includes an associated due date, due time, and task data. The processing circuit is further structure to provide a user interface having one or more indicators associated with each of the one or more tasks to a user of the staff computing device, where the indicators provide an indication of a completion status of each task based on the due date and due time of the task. The processing circuit is also structured to determine that at least one of the one or more tasks has been completed.

In various embodiments, the device data is received from at least one of an RFID reader and quick response (QR) code scanner of the staff computing device. In some embodiments, the processing circuit is further structured to provide, via the network interface, the task data associated with the at least one task of the one or more tasks that has been completed to the server computing device. In other embodiments, the patient data includes at least one of a room number, a name, and at date of birth of the patient. In yet other embodiments, the processing circuit is further structured to provide a patient representation on the user interface, generate and dispose a device representation based on the device data on the patient representation, and update a color of the device representation based on the task due date and due time. In various embodiments, the processing circuit is further structured to receive a request to generate a custom report, where the request including one or more data inputs specifying report data to be included within the custom report and a requesting party address, generate the custom report based on the one or more data inputs, and provide the custom report to the requesting party address. In other embodiments, the request to generate the custom report is received from a user interface generated and displayed by the staff computing device, where the user interface includes at least one of a drop down box and a plurality of check boxes through which the user can select the one or more data inputs of the request. In yet other embodiments, the requesting party address is related to the user interface, and the custom report is provided to the requesting party address related to the user interface to then generate a chart that is displayed to the user via the user interface.

Yet another aspect of the present disclosure relates to a non-transitory computer readable medium having computer-executable instructions embodied therein that, when executed by at least one processor of a computing system, cause the computing system to perform operations to generate and manage one or more tasks associated with a medical device. The operations include receiving patient data associated with a patient, receiving device data associated with the medical device, and generating one or more tasks based on the device data, where each task includes an associated due date, due time, and task data. The operations further include generating and providing one or more indicators based on each task of the one or more tasks to a user of a computing device, where the indicators provide an indication of a completion status of each task of the one or more tasks based on the due date and due time associated with each task. The operations also include determining that at least one of the one or more tasks has been completed.

In various embodiments, the patient data includes at least one of a room number, a name, and a date of birth of the patient. In some embodiments, the medical device includes a first disposable medical device and the operations further include receiving device data associated with a second disposable medical device, where the first disposable medical device and the second disposable medical device are the same device type. The operations also include determining, based on the first disposable medical device and the second disposable medical device being the same device type, that the one or more tasks have been completed. In other embodiments, the operations further include authenticating the user of the computing device as a staff member prior to allowing access to the computing device.

BRIEF DESCRIPTION OF THE FIGURES

FIG. 3 is a flow diagram of a method of generating and managing one or more tasks relating to one or more medical devices, according to an example embodiment.

FIGS. 4-8 are illustrations of a user interface that may be generated and displayed on a computing device used in connection with the workflow management application of FIG. 2 and the method of FIG. 3, according to an example embodiment.

FIG. 25 is a flow diagram of a method of adding patient data to an electronic health record of the patient by the workflow management application of FIG. 2, according to an example embodiment.

DETAILED DESCRIPTION

Figure 1:
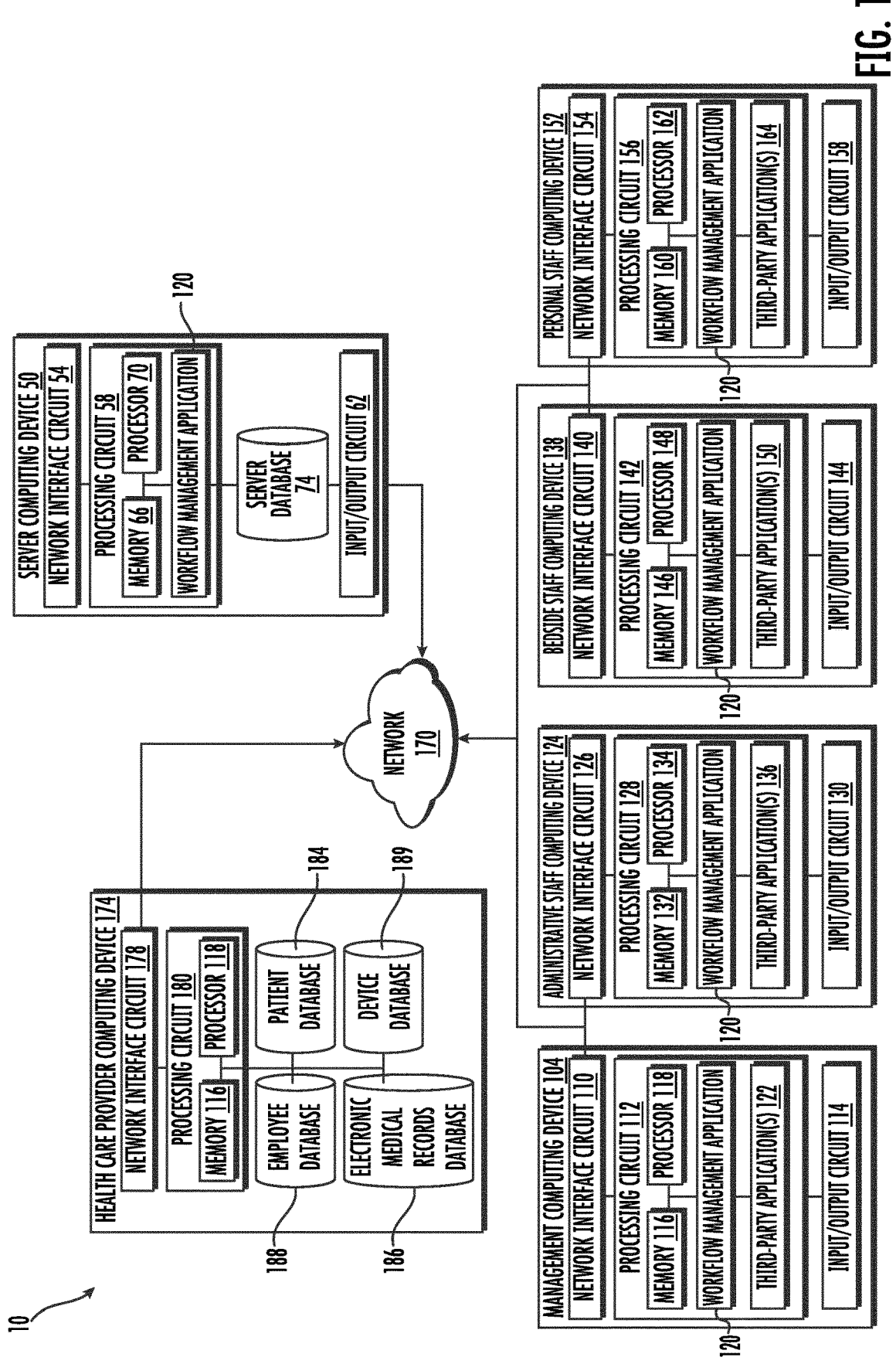
FIG. 1 is a component diagram of a medical device task generation and management system, according to an example embodiment.

Referring generally to the figures, systems and methods for medical device task generation and management are disclosed. The systems and methods described herein may enhance the generation and management of medical device tasks by utilizing a large amount of data to generate and personalize the tasks. For example, because tasks may be generated using various preferences of the staff member, device data, device preferences, and system preferences, the tasks may be customized to the health care provider and allow for better monitoring and tracking of the tasks themselves. Additionally, because the health care provider can set many preferences relating to the tasks and the devices, the health care provider can ensure that correct protocols are being followed throughout the entire health care provider system and manage and track compliance to protocol.

The embodiments of the medical device task generation and management system as described herein improve medical computing devices by performing certain steps that cannot be done by conventional medical computing devices or human actors. For example, the medical device task generation and management system generates a large amount of data from the completion of the tasks and analyzes the data to provide up to date statistics to multiple staff members of the health care provider. Additionally, the medical device task generation and management system provides real-time statistics relating to medical device inventory, medical device task compliance, staff member specific statistics, and management reports. In this way, users of the medical device task generation and management system can better generate and utilize the data relating to the medical tasks for various staff members of the health care provider, including but not limited to workflow improvements, compliance, increased patient/family satisfaction, etc.

The embodiments of the medical device task generation and management system may utilize a QR code, RFID tag, or barcode to generate and/or retrieve data relating to a medical device and/or a patient. By doing so, the medical device task generation and management system may provide a more streamlined and simpler intake process for both patients and medical devices. Additionally, because the medical device task generation and management system may update the patient's electronic health record based on the generated task and patient data, the medical device task generation and management system further simplifies the hospital intake system, allowing the staff member to simply scan the medical device to determine one or more pieces of patient data and then upload that data into the patients electronic health record.

The task, device, and patient data may also be made more secure by utilizing authentication measures that may require a user to use biometric data as well as other multi-level servicer authentication operations as described further herein.

Before turning to the figures, which illustrate certain example embodiments in detail, it should be understood that the present disclosure is not limited to the details or methodology set forth in the description or illustrated in the figures. It should also be understood that the terminology used herein is for the purpose of description only and should not be regarded as limiting.

Referring to FIG. 1, a component diagram of a medical device task generation and management system 10 for generating, managing, and analyzing the workflow of one or more healthcare devices is shown according to one embodiment. The medical device task generation and management system 10 generates one or more tasks associated with a healthcare device and then monitors and tracks the progress of each task. Further, the medical device task generation and management system 10 can analyze various data related to each task to be used as actionable data (e.g., reports) and to be stored within electronic medical records (EMR) of the corresponding patient. In some embodiments, the medical device task generation and management system 10 further provides useful records that can be used by management, administrative staff (purchasing, shipping, human resources, etc.), and bedside staff (e.g., direct patient care staff).

As shown in FIG. 1, the medical device task generation and management system 10 includes a server computing system 50, one or more management computing devices 104, one or more administrative staff computing devices 124, one or more bedside computing devices 138, one or more personal staff computing devices 152, and a health care provider computing device 174. While FIG. 1, shows one computing device 104, one computing device 124, one computing device 138, and one computing device 152, more or fewer devices may be utilized depending on the staffing levels of a health care provider (e.g., a hospital, a group of hospitals, a clinic, etc.). In other embodiments, certain components may be omitted. For example, a health care provider may not allow staff members to use personal computing devices while working, and therefore the workflow management computing system 10 may omit personal staff computing devices 152. The server computing system 50, the one or more management computing devices 104, the one or more administrative staff computing devices 124, the one or more bedside computing devices 138, the one or more personal staff computing devices 152, and/or the health care provider computing device 174, are in communication with each other and are connected by a network 170. As a result, the server computing device may include a network interface circuit 54, a processing circuit 58, and an input/output circuit 62.

As shown, the network interface circuit 54 is structured to establish connections with any of the one or more management computing devices 104, the one or more administrative staff computing devices 124, the one or more bedside computing devices 138, the one or more personal staff computing devices 152, and/or the health care provider computing device 174 by way of the network 170. The network interface circuit 54 includes programming and/or hardware-based components that connect the server computing system 50 to the network 170. For example, the network interface circuit 54 may include any combination of a wireless network transceiver (e.g., a cellular modem, a Bluetooth transceiver, a Wi-Fi transceiver) and/or a wired network transceiver (e.g., an Ethernet transceiver). In some arrangements, the network interface circuit 54 includes the hardware and machine-readable media structured to support communication over multiple channels of data communication (e.g., wireless, Bluetooth, near-field communication, etc.) Further, in some arrangements, the network interface circuit 54 includes cryptography module(s) to establish a secure communication session (e.g., using the IPSec protocol or similar protocol) in which data communicated over the session is encrypted and securely transmitted.

To support the features of the server computing system 50, the network interface circuit 54 may provide a relatively high-speed link to the network 170, which may be any combination of a local area network (LAN), an intranet (e.g., a private banking or retailer network), the Internet, or any other suitable communications network, directly or through another interface.

The processing circuit 58, as shown, comprises a memory 66, a processor 70, a medical workflow management application 120, and a server database 74. The memory 66 includes one or more memory devices (e.g., RAM, NVRAM, ROM, Flash Memory, hard disk storage) that store data and/or computer code for facilitating the various processes described herein. That is, in operation and use, the memory 66 stores at least portions of instructions and data for execution by the processor 70 to control the processing circuit 58. The memory 66 may be or include tangible, non-transient volatile memory and/or non-volatile memory. The processor 70 may be implemented as a general-purpose processor, an application specific integrated circuit (ASIC), one or more field programmable gate arrays (FPGAs), a digital signal processor (DSP), a group of processing components, or other suitable electronic processing components. The server database 74 may be structured to store, hold, access, and provide various types of data stored therein. In some embodiments, the server database 74 may be implemented as a part of the memory 66. In other embodiments, the server database 74 and the server computing system 50 may be implemented over the cloud (e.g., as cloud computing server and a cloud computing database).

The server computing system 50, as shown, is configured to run a variety of application programs and store associated data in a database of the memory 116. One such application may be a medical workflow management application 120. The workflow management application 120 includes computer-executable code stored in the memory 66. The workflow management application 120 is structured to be used in combination with a healthcare staff computing device (e.g., the one or more management computing devices 104, the one or more administrative staff computing devices 124, the one or more bedside computing devices 138, the one or more personal staff computing devices 152, and/or the health care provider computing device 174) to generate, manage, and process tasks associated with various healthcare devices. When executed on the server computing device, the workflow management application 120 may be used to process communications, provide functionality, and otherwise process requests of multiple other workflow management applications 120 that are implemented on other computing devices. In some embodiments, the workflow management application 120 may also store and retrieve data within the server database 74 received from or provided to the other workflow management applications 120. For example, the server database 74 may include one or more health care provider specific tasks that are associated with multiple healthcare devices and may act as a lookup table that provides relevant tasks to a requesting workflow management application 120.

The input/output circuit 62 is structured to receive communications from and provide communications to the user of the server computing system 50. In this regard, the input/output circuit 62 is structured to exchange data, communications, instructions, etc. with an input/output component of the server computing system 50. Accordingly, in one embodiment, the input/output circuit 62 is or includes an input/output device, such as a touchscreen. In another embodiment, the input/output circuit 62 includes communication circuitry for facilitating the exchange of data, values, messages, and the like between an input/output device and the components of the server 50. In yet another embodiment, the input/output circuit 62 includes machine-readable media for facilitating the exchange of data between an input/output device and the components of the server computing system 50. In still another embodiment, the input/output circuit 62 includes any combination of hardware components, communication circuitry, and machine-readable media. Hardware components can include a touchscreen, a keypad, microphone, camera, buttons, or similar components or combinations thereof, for receiving user inputs. Components of the input/output circuit 62 display or otherwise provide instructions, status notification and other data to the user. The display may be configured to display graphics such as menus, instructions, background, logos, and so on. In other embodiments, the server computing system 50 may not include an input/output circuit 62.

The server computing system 50, the health care provider computing device 174, the management computing device 104, the administrative staff computing staff device 124, the bedside staff computing device 138, and the personal staff computing device 152 as shown may be any suitable computing device. For example, the server computing system 50 and the health care provider computing device 174 may be server computing devices that act as the back end (e.g., supply the processing power, complete calculations, receive and provide requested data, etc.) to the workflow management application 120. Similarly, each computing device 104, 124, 138, and 152 may be a mobile phone, a personal computer (e.g., a desktop computer or a laptop computer), a tablet, a wearable device (e.g., a smart watch), an augmented reality device, or any other suitable user computing device capable of accessing and communicating using local and/or global networks. Additionally, the type of staff (e.g., management, administrative staff, etc.) may not be decided solely on the computing device but on the username and password within which each logs in to the device or into the workflow management application 120. In this way, the type of computing device (e.g., the management computing device 104) may be decided by the occupation of the user of said device, but each device may otherwise be generally the same.

Each of the staff computing devices (i.e., the management computing device 104, the administrative staff computing staff device 124, the bedside staff computing device 138, and the personal staff computing device 152) may include a processing circuit (e.g., a processing circuit 112, 128, 142, and 156), a network interface circuit (e.g., a network interface circuit 110, 126, 140, and 154), and an input/output circuit (e.g., an input/output circuit 114, 130, 144, and 158).

The processing circuits, the network interface circuits, and the input/output circuits may function substantially similar to and include the same or similar components as the processing circuit 58, the network interface circuit 54, and the input/output circuit 62 described above, with reference to the server 50. Accordingly, it will be understood that the description of the processing circuit 58, the network interface circuit 54 and the input/output circuit 62 provided above may be applied to the processing circuits (112, 126, 140, and 154), the network interface circuits (110, 126, 140, and 154), and the input/output circuits (114, 130, 144, and 158) of the staff computing devices. In some embodiments, the input/output circuits 114, 130, 144, and 158 may include a camera (e.g., standard, ultra-wide, telephoto) and/or a scanner. These devices may be structured to scan or capture images (e.g., a quick response (QR) code) and/or a document. In other embodiments, the input/output circuits 114, 130, 144, and 158 may further include a radio frequency identification (RFID) reader that may be configured to read or scan low or high frequency radio communications. In some embodiments, the RFID reader may be configured to capture near field communications (NFC) tags.

Referring now specifically to the bedside staff computing device 138, the processing circuit 142, as shown, includes a memory 146, a processor 148, the workflow management application 120, and one or more third-party applications 150. The bedside staff computing device 138 is configured to run a variety of application programs and store associated data in a database of the memory 146. One such application may be the workflow management application 120. The workflow management application 120 and the bedside staff computing device 138 are structured to be used within a healthcare patient's bedroom (e.g., at or near the bed) by the staff who handle the various tasks and cares (e.g., rolling a patient over, moving a patient, changing a patient's catheter, washing a patient, brushing a patient's teeth, etc.) of the patient. As such, the workflow management application 120 may be structured or configured to receive data relating to one or more healthcare devices and to generate one or more tasks associated with each device. For example, a bedside healthcare worker (e.g., a nurse, a certified nursing assistant (CNA), etc.) may be in the room of a patient and be about to install a healthcare device such as a catheter into the patient. Before doing so, the patient may use the bedside staff computing device 138, launch the workflow management application 120 and scan the catheter (e.g., a QR code on the packaging of the catheter) via the input/output circuit 144. By scanning the catheter, the workflow management application 120 may receive data relating to the catheter (e.g., expiration date, name of the device, specifications of the device, etc.) and may then add the device to a profile for the patient within the workflow management application 120.

Once the device (e.g., the catheter) is added to a profile for the patient within the workflow management application 120, the workflow management application 120 may generate or determine tasks (e.g., changing the catheter every 2 hours, cleaning the catheter every 6 hours, etc.) associated with the device, each task including a date due and a time due and then generate one or more reminders or indicators based on the task. The reminders or indicators may be a variety of different displays or notifications that may be provided to a user (e.g., the staff member) of the bedside staff computing device 138 to remind them or indicate that the task is or will be due. Additionally, each task may include multiple reminders or indicators (e.g., 2 hours until due, 1 hour until due, due, overdue, etc.). For example, the reminders may be provided as notifications that pop up on the screens of one or more staff computing devices (e.g., the management computing device 104, the bedside computing device 138, etc.) based on a relationship to the patient that the device is being used on. For example, the reminders may be provided only to the staff members that are responsible for the patient. In other embodiments, the reminders may be available to all staff members but only directly provided to the staff members that are responsible for the patient. In other embodiments, the reminders may be provided via the input/output circuit 130 as part of a user interface that is presented to the user via a display. The display may be provided to the bedside staff member (or another user of the bedside staff computing device 138 (e.g., a doctor that is at the bedside staff computing device 138)) and show the user interface including the reminders to provide a quick understanding of the tasks that are at or past their due date and time due, or tasks that are still approaching their due data and time due. In this way, the indicators of the workflow management application 120 may provide the user with an automatically generated and quick to decipher indication of what tasks the bedside staff member should perform while in the patient's room.

Still referring to FIG. 1, the workflow management application 120 may further include an option (e.g., via the input/output circuit 130) to indicate that a specified task(s) is completed. Once the task is completed, the workflow management application 120 may store the task data (e.g., type of task, date and time completed, due date and time, the patient data (e.g., the patient who had the task completed, the EMR of the patient, etc.) associated with the task, the staff data (e.g., the staff member who completed the task, etc.) associated with the task, and/or the device data (the type of device used, the quantity of the devices used, etc.) associated with the task. For example, when the task is indicated as being completed, the workflow management application 120 may record that it is completed within the memory 146 and/or within the server database 74 or server memory 66 (so all of the workflow management applications 120 show the task as completed). Then, the workflow management application 120 may generate one or more new tasks based on the same medical device. In some embodiments, the workflow management application 120 may keep track of the number of completed tasks for each device and also generate one or more tasks to replace the device or take other action. For example, the workflow management application 120 may know or lookup (from internal code, from a database having hospital policy (e.g., the server database 74), etc.) that the catheter must be replaced after being cleaned three times or every day (whichever comes first), and therefore, after the third time being cleaned, the workflow management application 120 may generate a task to replace the catheter. Once the task is marked as complete and a new catheter is received for the patient, the workflow management application 120 may then store data relating to the catheter (as well as the completion of that task).

In some embodiments, if the task is not marked as complete, the workflow management application 120 may generate and provide an alert to one or more staff members based on the task. The alerts may differ from the reminders in that they are provided to more staff members as well as higher level staff members. For example, a reminder may be only provided to a bedside staff member, whereas the alert may be provided to the manager of the bedside staff member, or the manager's boss, etc. In other embodiments, the reminders simply provide a visual reminder to complete the task when the workflow management application 120 is open, and the alerts provide a visual and an audio reminder to complete the task (even when the workflow management application 120 is not open).

In some embodiments, the processing circuit 128 includes one or more third party applications 136. Generally, the one or more third party applications 136 may be an application provided by a third party entity (e.g., an entity that is not related to the workflow management application 120). For example, third party application 136 may be an application for social media, various health system related applications, etc.

The management computing device 104 may be the computing device of one or more managers within the health care provider (e.g., doctor, surgeon, nurse-practitioner, etc.) and includes the network interface circuit 110, the processing circuit 112, and the input/output circuit 114 as described herein. The processing circuit 112 includes a memory 116 and a processor 118. The management computing device 104 is configured to run a variety of application programs and store associated data in a database of the memory 116. Two such applications may be a third party application 122 (similar to the third party application 136) and the workflow management application 120. The workflow management application 120 may perform essentially the same functions as the workflow management application 120 of the bedside staff computing device 138. For example, the management staff may be able to add patients, devices, and manage tasks via the workflow management application 120. Additionally, the management staff of the management computing device 104 may further use the workflow management application 120 to determine analytics/statistics specific to the manager/ the unit that the manager manages. As described herein, the workflow management application 120 stores task data of the completed tasks, device data, and, in some embodiments, patient data. The workflow management application 120 may further be structured or configured to generate statics relating to the manager via the workflow management application 120. For example, the manager may request statistics of their unit (e.g., all patients located in specific room numbers or under the care of certain staff members) for the day relating to a certain type of device (e.g., catheters). An example set of returned statistics may then display how many tasks for catheters within the manager's unit were completed on time, how many tasks were completed late, how many tasks were not performed, how many total catheter's the unit used, etc. In this way, the manager may even be able to determine compliance/noncompliance (e.g., did the unit perform the required tasks, a certain number/ percentage of non-required tasks, etc.) of their specific unit based on the statistics.

The administrative staff computing device 124 may be the computing device of one or more administrative staff (e.g., purchasing, human resources (HR), facilities manager, etc.) within the health care provider and includes the network interface circuit 126, the processing circuit 128, and the input/output circuit 130. The processing circuit 128 includes a memory 132 and a processor 134. The administrative staff computing device 124 is configured to run a variety of application programs and store associated data in a database of the memory 132. Two such applications may be the third party application 136 and the workflow management application 120. The workflow management application 120 may perform essentially the same functions as the workflow management application 120 of the bedside staff computing device 138 and the management computing device 104. For example, the administrative staff may be able to add patients, devices, and manage patient/device tasks via the workflow management application 120. Additionally, the administrative staff of the administrative staff computing device 124 may further use the workflow management application 120 to determine analytics/statistics specific to various healthcare devices. As described herein, the workflow management application 120 device data may then be used by the administrative staff. For example, the workflow management application 120 may be configured to generate usage statistics for each or all of the various healthcare devices via the workflow management application 120. For example, a purchasing staff member may request statistics on how many catheters the health care provider used in the past month. An example set of returned statistics may include the various types and numbers of catheters that were used, the total number of used catheters, the total number of catheters in stock, and, in some embodiments, an estimate of how many catheters the health care provider will use in the next month. In this way, the administrative staff (the purchasing staff in this situation) can better determine total stock and plan purchasing based on various requested statistics.

The personal staff computing device 152 may be a personal device (e.g., a personal cell phone, personal smart watch, etc.) of a staff member (any staff member described above) and includes the network interface circuit 154, the processing circuit 156, and the input/output circuit 158. The processing circuit 156 includes a memory 160 and a processor 162. The personal staff computing device 152 is configured to run a variety of application programs and store associated data in a database of the memory 162. Two such applications may be a third party application 164 (similar to the third party application 150) and the workflow management application 120. The workflow management application 120 may perform essentially the same functions as the workflow management application 120 of the bedside staff computing device 138, the management computing device 104, and the administrative staff computing device. For example, staff may be able to add patients, devices, and manage patient/device tasks via the workflow management application 120. In some embodiments, the workflow management application 120 of the personal staff computing device 152 may be used for the staff member to check various tasks during off times (e.g., lunch, break, etc.). In other embodiments, the workflow management application 120 may be used on a personal staff computing device 152 in situations where there is no dedicated staff computing devices (e.g., at-home care, remove care, etc.). In further embodiments, the health care provider may prevent the workflow management application 120 from being downloaded or installed on personal devices.

As described herein, the type of computing device (i.e., the management computing device 104 is known to be operated by management) is determined based on the computer being password protected and being logged into by the specific staff member. For example, a computer that is used within a patient's room (e.g., at the bedside) that is logged into by management is a management computing device 104. In other embodiments, the workflow management application 120 may further require authentication (e.g., a username and a password requirement) before allowing the user of a computer to access the workflow management application 120. In other embodiments, further authentication may be required to see certain portions of the workflow management application 120 (e.g., the unit statistics described herein) but not others (e.g., adding a patient and a device to the patient as described herein). In even other embodiments, authentication may allow for customization of the workflow management application 120. For example, an authenticated purchasing staff member may customize the workflow management application 120 to directly open to statistics on inventory of devices, and an authenticated bedside staff member may customize the workflow management application 120 to directly open to indicators relating to patients of the bedside staff member or the hospital system protocol.

The health care provider computing device 174 may be similar to the server computing system 50 (in some embodiments, the server computing device may be integrated within the health care provider computing device 174) and act as a server for the health care provider. To do so, the health care provider computing device may include a network interface circuit 178, a processing circuit 180, a patient database 184, an electronic medical records (EMR) database 186, an employee database 188, and a device database 189. In some embodiments, one or more of the databases may be implemented within a single database (e.g., within a single cloud database). The processing circuit 180 and the network interface circuit 178 may function substantially similar to and include the same or similar components as the processing circuit 58 and the network interface circuit 54 described above with reference to the server 50. Accordingly, it will be understood that the description of the processing circuit 58 and the network interface circuit 54 provided above may be applied to the processing circuit 180 and the network interface circuit 178. In use, the health care provider computing device 174 may interface, via the network, with various third party applications and the workflow management application 120 to provide and receive various requested pieces of data. For example, the device database 189 may include data relating to various different devices within the hospital, and specific tasks, requirements, or protocols associated with each. Similarly, the patient database 184 may include names, room numbers, and other data specific to patients that the workflow management application 120 may request to perform different functions. In one example, the workflow management application 120 may provide patient specific data to the patient database 184. Similarly, the employee database, may store data related to each employee (e.g., permissions for each employee, units for each employee, employee salary, etc.). Lastly, the EMR database 186 may include all of the EMR of the patients who have used the health care provider. By doing so, the workflow management application 120 has a large amount of data it can access to better generate, track, etc. the various device tasks.

Figure 2:
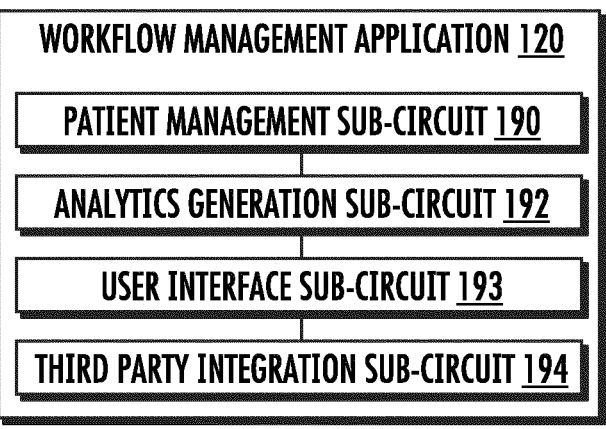
FIG. 2 is a block diagram of a medical workflow management application of the medical device task generation and management system of FIG. 1, according to an example embodiment.

Referring now to FIG. 2, the medical workflow management application 120 is shown in more detail according to one embodiment. The workflow management application 120 may include one or more sub-circuits that use the memory and the processor of the specific computing device to perform one or more tasks. In one embodiment, the workflow management application 120 includes a patient management sub-circuit 190, an analytics generation sub-circuit 192, a user interface sub-circuit 193, and a third party integration sub-circuit 194. While referred to as sub-circuits, the patient management sub-circuit 190, the analytics generation sub-circuit 192, the user interface sub-circuit 193, and the third party integration sub-circuit 194 may be structured as full circuits, each having a dedicated memory and processor.

In one embodiment, the patient management sub-circuit 190 is configured to handle tasks associated with a patient, such as generating one or more tasks based on device data and then handling the tasks during the lifetime of the tasks. As such, the patient management sub-circuit 190 may be communicably coupled to one or both of the device database 189 and the server database 74 (e.g., via the network 170 and the respective network interface circuit) to receive one or more tasks associated with each device. In one embodiment, the patient management sub-circuit 190 may further include one or more hard coded tasks (e.g., tasks that are automatically included within the patient management sub-circuit 190) that are used if the device database 189 or the server database 74 do not have any tasks associated with the respective device. In this way, the device database 189 or the server database 74 may include client specific tasks associated with each device and the patient management sub-circuit 190 may include generic tasks associated with each device. In another embodiment, the patient management sub-circuit 190 may allow a user of the workflow management application 120 to enter new devices or new tasks associated with a certain device, edit tasks or devices, or delete tasks or devices. In some embodiments, a user may have to be authenticated and authorized (e.g., as management) prior to doing so. In further embodiments, a user of the workflow management application 120 may be able to add one or more tasks that are not associated with any devices at all. For example, the user may be able to generate one or more tasks to wash the patient every eight hours (without specifying any specific medical washing devices). Additionally, the patient management sub-circuit 190 is communicably coupled to the network 170 (via the respective network interface circuit) and the other components of the processing circuit 142 to receive and update the current date and time. Because all of the tasks include a due date and a time due, the current date and time is used by the patient management sub-circuit 190 to determine all of the due dates and time dues for the multiple tasks. Additionally, the current date and time is used to determine when the indicators and the alerts should be generated or provided to the display. In this way, the patient management sub-circuit 190 may work directly with the user interface sub-circuit 193 to generate and or display the indicators and the alerts if necessary.

The analytics generation sub-circuit 192 is structured or configured to generate one or more statistics or analytics (based on the data available to the analytics generation sub-circuit 192) and provide the statistics in various output forms. The analytics generation sub-circuit 192 may be communicably coupled to one or more of the user interface sub-circuit 193, the patient database 184, the EMR database 186, the employee database 188, the device database 189, the server database 74, the respective input/output circuit, and the respective memory. In this way, analytics generation sub-circuit 192 may be configured to receive one or more requests (e.g., via the input/output circuit or the user interface sub-circuit 193) to process data and generate statistics (processed data) based on the requests. For example, analytics generation sub-circuit 192 may be configured to receive, via the user interface sub-circuit 193, a request to process the device data (e.g., of the device database 189, the server database 74, and/or the respective memory of the computing device) and generate statistics showing usage of catheters per day over a month. The analytics generation sub-circuit 192 may request the device data, receive the device data, process the device data based on the request and inputs included with the request, and provide the device data to the requesting party (e.g., the user interface sub-circuit 193). In this way, the analytics generation sub-circuit 192 may be specifically configured to perform high speed data processing, preventing the other sub-circuits from having to do any calculation intensive data processing, and generally speeding up the operation of the workflow management application 120.

The user interface sub-circuit 193 is configured to interface with the respective input/output circuit and generate an interactive user interface via a display. While the capabilities of the user interface will be described further herein, the user interface sub-circuit 193 is configured to handle the various functions, generation of pages, and capability of the user interface. Additionally, the user interface sub-circuit 193 is communicably coupled to all of the other sub-circuits to provide user input and generate user output of the respective computing device. By doing so, the other sub-circuits can focus on the back-end of the workflow management application 120, and the user interface sub-circuit 193 can focus on the front-end of the application 120.

The third party integration sub-circuit 194 is structured or configured to interface with various third party applications (e.g., the third party applications 122, 136, 150, and 164) to exchange data or data. More specifically, the third party integration sub-circuit 194 is configured to interface with a third party application that operates in conjunction with the electronic medical records database 186 to receive and update the EMR of specific patients. In one embodiment, the third party integration sub-circuit 194 may be configured to interface (e.g., via an application programming interface (API)) with Redox® to receive and provide updates to the EMR of specific patients. Redox® is a cloud-based electronic health record (EHR) application that is configured to store, monitor, and handle the EMR of patients. By interfacing with Redox®, via the Redox® API, the third party integration sub-circuit 194 allows the workflow management application 120 to consistently update the EMR of a patient based on the data generated during the normal operation of the workflow management application 120. In some embodiments, the third party integration sub-circuit 194 may work with other third party applications, including other EHR applications, and other third party applications altogether.

Referring to FIG. 3, a flow diagram of method 200 for generating and managing one or more medical device tasks is shown, according to an example embodiment. Operations of the method 200 may be conducted by the medical device task generation and management system 10 (e.g., the patient management sub-circuit 190 of the workflow management application 120 of one of the one or more management computing devices 104, the one or more administrative staff computing devices 124, the one or more bedside staff computing devices 138, and/or the one or more personal staff computing devices 152). Through the steps of the method 200, the respective staff computing devices, generate or determine one or more tasks relating to a medical device and manage the various tasks based on user input.

As shown, the method 200 commences at step 204 in which one of the computing devices (e.g., the one or more bedside staff computing devices 138) receives patient data. In some embodiments, the health care provider computing device 174 may provide the patient data (e.g., via the patient database 184) to the respective staff computing device. In another embodiment, the patient data may be entered by intake staff (e.g., via the respective input/output circuit 144) into the workflow management application 120. As described herein, "patient data" may be any data regarding the respective patient. For example patient data may include a name, address, date of birth, attending physician, staff member in charge of the patient, physical description of the patient, room number, unit number, medical condition/reason for being in-taken, or any combination thereof. In some embodiments, patient data is simply a room number and does not include any personal details of the patient. In this way, the patient data is not considered medical records that are protected under the Health Insurance Portability and Accountability Act (HIPAA) and does not need to be encrypted or kept entirely confidential. In another embodiment, patient data includes data that is protected under HIPAA and is encrypted or otherwise stored under the guidance provided by HIPAA. In one example, a CNA logged into the bedside staff computing device 138 may intake a new patient and enter them into the workflow management application 120 (e.g., via a user interface) by adding a new room number. Once added, the workflow management application 120 may then know that there are potential tasks that may be further added to the room. In some embodiments, tasks may be automatically added once the patient is added to the room (e.g., initial nurse patient-check, collect insurance data, etc.). In other embodiments, step 204 may be combined with a step 212 (which will be described further herein) and the patient data may be received with/at the same time as the device data.

Once the patient data has been received, the method 200 proceeds to a step 208 in which a patient profile is generated based on the patient data. In some embodiments, method 200 may proceed directly to step 212 (i.e., skip step 208) and no patient profile is created. In other embodiments, the workflow management application 120 may generate a patient profile that includes the patient data and can be used if the patient ever returns to the health care provider. For example, the patient profile may include the patient data, but also include a health history of the patient such that the bedside staff can see previous tasks that were completed with respect to the patient and other data that the workflow management application 120 may have. In some embodiments, to determine that the patient data corresponds to a previously generated patient profile, the workflow management application 120 may require or request multiple pieces of patient data (e.g., date of birth and name) and not just a single piece of patient data. If only provided one piece of patient data, the method 200 may generate a new patient profile for the patient and proceed to step 212.

After the patient profile has been generated, the method 200 proceeds to step 212 at which device data is received. As described herein, device data may be received via the respective input/output circuit (e.g., the input/output circuit 144), via the camera or a RFID reader. For example, the user of the bedside staff computing device 138 may launch the workflow management application 120 and (via the user interface) indicate they would like to add a medical device to a patient. Once indicated, the workflow management application 120 may launch the camera of the bedside staff computing device 138 and allow the input/output circuit 144 to read a QR or bar code of the medical device (e.g., on a wrapping or cover of the medical device). Once read, the input/output circuit 144 may generate or determine device data from the bar/QR code. In another embodiment and once indicated, the workflow management application 120 may launch an RFID reader of the input/output circuit 144 to read an RFID tag or NFC chip of the medical device. By reading the RFID tag or NFC chip, the input/output circuit 144 may generate or determine device data. In devices where there is no QR code, bar code, RFID tag, or NFC chip, the workflow management application 120 may include an option to manually enter device data (e.g., via the keyboard or the display of the input/output circuit 144). As described herein, "device data" may refer to data relating to or describing the device. For example, device data may include a serial number, a model number, a model name, an internal product or device number, a general product number, a device name, one or more specifications of the device (e.g., ¼ inch diameter), or a generic device name (e.g., "cast"). In this way, one or more types of device data may be generated or determined by the workflow management application 120 or the input/output circuit 144. For example, the QR code, when read, may simply provide a serial number. The input/output circuit 144 may provide the serial number to the workflow management application 120 which may then lookup the serial number in the device database 189, the server database 74, or the respective memory (e.g., the memory 146). From there, the workflow management application 120 may then receive multiple pieces of device data which can be used to generate tasks.

Once the device data has been received, the method 200 may proceed to step 214 and add the device data to the patient's profile. In some embodiments (in which there is no patient profile), the method 200 may skip step 214 and proceed to step 216. At step 214, the device data is added to the patient profile such that it can be readily viewed and accessed via the patient profile. In some embodiments, the patient profile may further include data such as time stamps of when the device data was added to the patient profile.

After the device data has been added to the patient's profile, the method 200 proceeds to step 216 in which one or more tasks are determined or generated based on the device data, each task including a task due date and a task time due. In some embodiments, as described herein, the one or more tasks may be determined through a lookup table (e.g., the device database 189 or the server database 74) which may be decided based on the task protocols of the healthcare provider. As used herein, the "task protocols" refer to each of the tasks that are automatically generated for a specific device and the task due date and due time for each task which can be either decided solely by the healthcare provider or by the healthcare provider in combination with the user. For example, the workflow management application 120 may receive the device data at step 212 and then provide the device data to the device database 189 or the server database 74 which may then return one or more preprogrammed tasks that are associated with the device data as indicated by the task protocols. In this way, the tasks may be health care provider specific and set by the health care provider itself. In other embodiments, the server database 74 may include one or more generic tasks that are associated with the device data. For example, the device data may include a serial code that relates to a wheelchair. The wheelchair may come with built in tasks such as clean the wheelchair every 4 hours, check that the wheelchair wheels are locked every 1 hour, and put the wheelchair within arm's reach at 9 PM every night. By providing the device data to the server database 74, the server database 74 may return the built-in tasks associated with the device.

In other embodiments, the workflow management application 120 may generate the tasks using one or more methods. For example, the workflow management application 120 may receive the device data at step 212 and then process the device data to determine the one or more tasks associated with the device. In one embodiment, the workflow management application 120 may include one or more device types and one or more preprogrammed tasks associated with each device type. Therefore when the workflow management application 120 receives the device data, the workflow management application 120 may be configured to determine a device type based on the device data and generate the one or more tasks as a result. If the workflow management application 120 is not able to determine the device type based on the device data, the workflow management application 120 may indicate this to the user of the staff computing device and request they manually enter one or more tasks associated with the device. The workflow management application 120 may further allow the user to save these tasks (e.g., within the memory 146 or the server database 74) associated with the device data and may then generate the tasks automatically in response to the same device data being received. In this way, the workflow management application 120 may further allow for customization based on the staff member being authenticated as described above. As certain staff members may have preferred tasks, the staff members may be able to add these tasks (e.g., have the tasks saved in relation to the device data and their staff data within at least one or more of the memory 146, the server database 74, and the device database 189) and have the specific tasks created for themselves. In some embodiments, tasks may be added for a respective staff member but not removed (i.e., the staff member cannot remove the preassigned tasks but can add and remove new tasks).

In some embodiments, each device may generate or be associated with multiple tasks. For example, in the wheelchair described above, the wheelchair generated three tasks. In some embodiments, each device may generate a predefined number of tasks that culminate in a final task of replacing the device. In other embodiments, each device may include an infinite number of tasks that only end when the device must be replaced because it is broken or the patient has left the health care provider (e.g., the patient is discharged from the hospital). Again referring to the wheelchair, a patient who is provided a wheelchair will likely not have the wheelchair replaced in their time at the hospital (unless it is broken). In this way, the tasks vary based on the device data that is received at step 212. Additionally, each task may include a task date due and a time due. In some embodiments, the date due and time due is based on the current time and a number of hours the task must be completed within. In other embodiments, the due date and time due is a specific time every day, week, month, or year. For example, one task may be due every three hours and is therefore due three hours from the time the task is generated, and another task may be due every day at 9:00 PM (local time) and is therefore due at 9:00 PM regardless of other tasks, etc. In some embodiments, the tasks are further associated with a task type when generated. A task type may be based on the device data or the device type and further provide a way to organize the various tasks. In one example, the task type(s) may be associated with the device data (e.g., all of the tasks for the wheelchair are of the wheelchair tasks type).

Once the tasks have been generated or determined, the method 200 proceeds to step 220 at which one or more reminders are generated and provided based on each task. In some embodiments and as will be described further herein, the reminders may be generated on the user interface of the workflow management application 120. In other embodiments, the reminders may be alarms that are generated and sent through other means (e.g., email, phone call, text message, noise, etc.). The reminders may be indications of the situation (e.g., due in three hours or less, due in an hour or less, due, overdue, etc.) regarding each task. In further embodiments, the reminders may be generated and provided based on the staff member using the workflow management application 120. For example, one (authenticated) staff member may have the workflow management application 120 setup to generate and provide the user a reminder via text one hour before a task is due and at the time the task is due. In other embodiments, the reminders may be generated and provided based on the device data and the type of task. In further embodiments, the reminders may be provided to staff members based on various stored preferences, or to the user interface if no other preferences are stored. For example, a hospital may include preferences that reminders are provided to all staff member responsible for a patient but not their supervisor, and another hospital may include preferences that reminders are provided to all staff members responsible for a patient and their supervisor. Additionally, each task may generate multiple reminders. In the example described above (due in three hours or less, due in an hour or less, due, and overdue), a single task generated four separate reminders. In other embodiments, each task may generate 1, 2, 3, 4, or more reminders.

Once the reminders have been generated and provided, the method proceeds to a step 224 at which it is determined if the task is completed. In some embodiments, the task may be determined to be completed by receiving, from the input/output circuit (e.g., the input/output circuit 144), an indication that the task is completed. For example, a staff member may complete the task and indicate as such through the user interface and the display of the input/output circuit 144. In other embodiments, the task may be considered completed if device data is received that indicates that the task was completed. For example, the task may be to replace the previous medical device, and if the staff member provides new device data (related to the same type of device), the task may be considered completed. In other embodiments, the workflow management application 120 may require confirmation/verification (e.g., a virtual signature of the staff member, a virtual signature of the staff member's supervisor, etc.) that the task was completed before a task is considered completed. By doing so, the workflow management application 120 may improve accountability and prevent tasks from being marked completed if they have not been completed If it is determined that the task is not completed at step 224, the method 200 proceeds to step 228 at which one or more alerts are generated and provided based on the task. The alerts may be similar to the reminders, but indicate that a task is overdue (as compared to coming due) and are higher level reminders. For example, while the reminders may be relatively passive (e.g., provide data), the alerts may be assertive and force a staff member to take action with regard to the task. In one embodiment, the alerts may provide the reminders to higher level staff members. For example, while the reminders may be provided to the staff members responsible for the patient but not their supervisor (based on the preferences as described above), the alerts may also be provided to the supervisor. In another embodiment, the alerts may be provided in different ways from the reminders (to better reach the staff member). For example, the reminder may be solely provided via the user interface, and the alerts may be provided via the user interface, via sound, and via email. In this way, the workflow management application 120 better provides for accountability and helps to ensure that all tasks are completed.

If it is determined that the task is completed at step 224, the method proceeds to step 232, and the task data (e.g., timestamp the task completed, type of task, name of task, task due date and time due, etc.), the patient data, and/or the device data are stored. In some embodiments, step 232 may take place after every step (e.g., the workflow management application 120 constantly saves the data). In other embodiments, step 232 may take place in response to the user requesting the data to be saved. The data may be saved to a variety of places including the memory (e.g., the memory 146, the device database 189, the patient database 184, the employee database 188, the EMR database 186, and/or the server database 74). Additionally, while step 232 is shown to lead back to step 216, step 232 may lead to other steps (based on the task). For example, if the task was to remove and replace the medical device, step 232 may lead to 212 in which the new device data is received. In this way, step 232 is highly variable and may take place at many different times or places. Additionally, other data may also be saved during step 232. In one example, staff member preferences (e.g., additional tasks they want generated for specific device data, additional indicators, where to provide the indicator, etc.) may be saved during step 232.

Referring now to FIGS. 4-8, a user interface 300 that may be presented (e.g., via the display of the respective input/output circuit) to the user (e.g., during, before, and/or after the method 200 or the method 500) is shown, according to an example embodiment. The user interface 300 may be presented by any one of the computers having the workflow management application 120 (e.g., the management computing devices 104, the administrative staff computing devices 124, the bedside staff computing devices 138, the personal staff computing device, and the server computing system 50) via the respective input/output circuit. As will be described further herein, the user interface 300 may first generate a login screen or page within which the user of the workflow management application 120 must login or be authenticated to be able to use the full functionality of the workflow management application 120 (and the user interface 300). In some embodiments, the staff member/user must be authenticated by a username or password. In other embodiments, the staff member/user may be authenticated by biometric means (e.g., facial recognition, electrocardiogram (EKG), fingerprint, etc.), or by secondary authentication measures (e.g., one-time code). By doing so, the workflow management application 120 and the user interface 300 can receive and save one or more preferences relating to the respective staff member and also ensure that patient data within the workflow management application 120 is not able to be accessed by unknown parties. In even other embodiments, the computing device itself may require authentication but the workflow management application 120 may not.

The user interface 300 includes multiple pages (e.g., a first page 302, a second page 320, a third page 368) through which the user of the workflow management application 120 can interact with the various functions and capabilities of the workflow management application 120. In some embodiments, upon login, the user may first be presented with the first page 302. In other embodiments, the staff member may be able to input preferences that decide which page is first presented to the respective staff member (e.g., when authenticated as described herein). The first page 302 includes a profile button 308 that directs the user to an application profile of the user, a report button 312 that navigates the user to a report generation page, a notification button 316 that navigates the user to a notification page, multiple patient buttons 318 that each navigate the user to a patient management page, and a home button 324 that navigates the user to a home page.

The report button 312, the notification button 316, the multiple patient buttons 318, and the home button 324 are all buttons that are configured to perform a function when selected (e.g., clicked). For example, if the user of the workflow management application 120 wants to generate an analytical report (as will be described further herein), the user may select the report button 312 (e.g., via the touch-screen display or the keyboard). Similarly, the notification button 316 may be selected to provide the user with the one or more alerts or reminders (or other notifications) that the user may want to take action on. Lastly, the patient buttons 318 each include patient data (in this example, the room number of the patient) that when selected allows the user to navigate to the respective patient page. In some embodiments, the patient data may be generated from the patient profile. In other embodiments, the patient data may be provided prior to the patient buttons 318 including the data (e.g., are otherwise blank). In even other embodiments, the patient buttons 318 may always include a room number. Additionally the patient buttons 318 may include one or more visual indicators (e.g., color indications) about the status of the patient in the respective room. In the example shown, the patient buttons 318 are filled with the colors white, grey, yellow, or red. In some embodiments, if the patient button 318 is the color grey or white (e.g., a first color) it may indicate that no patient is within that room number (e.g., no patient data has been entered for that room), or it may indicate that a patient is within that room but no task is due. In other embodiments, if the patient button 318 is the color yellow (e.g., a second color), it may indicate that patient is within that room and a task is due (or will be due soon (i.e., under 10 minutes, etc.)). In some embodiments, if the patient button 318 is the color red (e.g., a third color) it may indicate that a task is due or is overdue.

If the user of the workflow management application 120 clicks or presses the patient button 318, the user interface may generate the second page 320 and display the second page 320 to the user via the user interface 300 (i.e., navigate the user to the second page 320) through the input/output circuit. As shown, the second page 320 may be patient specific and may therefore include the home button 324, a task button 328 that displays the one or more tasks relating to the patient, a patient header 332 that displays patient data, and a patient representation 336. In use, the second page 320 provides patient specific data (e.g., tasks, devices, etc.) that can be used to determine what (if any) tasks are due for that patient and therefore may be generated using the patient data as well as any task data associated with the patient. Furthermore, the user of the workflow management application 120 can add one or more devices to the specific patient and then use the second page 320 to manage the tasks and devices. In this way, the patient header 332 provides relevant pieces of the patient data (e.g., name, room number, etc.) such that the user can identify they are in the correct patient's room.

The home button 324 and the task button 328 perform one or more functions when clicked. For example, the home button 324 navigates (i.e., generates the home screen and/or puts the home screen as the page being displayed by the user interface) the patient to the home screen (e.g., the first page 302) which may be decided by the staff preferences. Similarly, the task button 328 causes a task list 356 to be displayed on the second page 320 such that the user can see the tasks that are due for the specific patient. The tasks button 328 therefore allows the user to more readily see and manage the one or more tasks of the specific patient.

In contrast, the patient representation 336 acts as both a button (in some embodiments) and an data display such that the user can select the patient representation 336 to perform one or more functions and can gather data from looking at the patient representation 336. In some embodiments, the user can provide device data to the workflow management application 120 (related to step 212) via the patient representation 336. For example if the user clicks the patient representation 336, the workflow management application 120 may launch the camera or the RFID reader of the input/output circuit to then add a device to the patient. In other embodiments, if the user clicks the patient representation, the workflow management application 120 may generate and display a pop-up in which the user can manually enter device data. Once the device is added, the one or more tasks related to the device and the visual reminders or indicators may be automatically generated or determined and placed on the second page 320.

Still referring to 5, the patient representation 336 is shown to include multiple device representations that provide a visual reminder or indication of tasks that are due, overdue, or upcoming for each device. For example the patient representation 336 may include a bedside device representation 338 with a green color visual indicator, a bedside turn assist device representation 340 with a green color visual indicator, a lower body device representation 342 with a yellow color visual indicator, an oral device representation 344 with a red color visual indicator, and a catheter device representation 346 with a grey color visual indicator (meaning that no catheter is in use on the patient). In this way, as soon as the devices are added at step 212, the workflow management application 120 may determine or generate the one or more tasks associated with each, generate the representation of the devices on the patient representation 336, and generate and apply the one or more visual indicators (e.g., change the color of the representations) to the patient representation 336. In this way, the user of the workflow management application 120 can look at the patient representation 336 and know what devices the patient is using and the status of the tasks associated with each. The visual indicators may use a stop-light coloring pattern (e.g., red, yellow, green) to provide a visual indication of the status of each tasks. For example, red may indicate that a task associated with the medical device (e.g., the bedside turn assist device representation 340) is overdue or is due, yellow may indicate that a task associated with the medical device is due, is about to be due (e.g., <1 hour until due), or that there is a task that is not yet due, and green may indicate that there is a task associated with the medical device but it is not due for a longer period of time (e.g., >1 hour) or that no task is due.

Referring to FIG. 6, each device representation may also be a clickable or otherwise selectable button such that the user can click each representation to be presented with one or more options. For example, FIG. 6 shows the catheter device representation 346 after it has been clicked or selected such that a status button 349 and a protocol button 350 are displayed on the second page 320 of the user interface 300. The status button 349 may allow the user to click the button and update the status of the device. For example, the user of the workflow management application 120 may be able to change the status of the device such that it is not in use or it is in use. In this way, the user may be able to add devices by clicking on the respective device representation and selecting the status button 349. In one example, the status button 349 may launch the camera or the RFID reader of the input/output circuit when clicked. The protocol button 350 will be discussed further with respect to FIG. 8, but may allow the user to see the health care provider specific protocol for the respective device. For example, if the user were to click the see protocol button 350 generated by clicking the catheter device representation 346, the user may be directed to the health care provider's protocol for handling and completing the tasks related to the catheter. The user may then close the protocol button 350 and the status button 349 by pressing a back button 325 or clicking on the second page 320 at a location that is not either the status button 349 or the protocol button 350.

To generate a list of the patient specific tasks and times each task is due, the user may then select the task button 328. When the task button 328 is selected, a task list 356 (see, e.g., FIG. 7) may be generated and displayed on the second page 320 of the user interface 300. The task list 356 may include device data 360, task type 364, and task due time 366 such that the user can look at the task list 356 and see what tasks are due for each device at what time. For example, the device data 360 may include and provide a visual representation of the device (e.g., a picture of the device, a title of the device, etc.) such that the user can look at the device data 360 and know which medical device has a task. Furthermore the task type 364 and the task due time 366 may provide a visual representation of the task and the time the task is due such that the user knows which task to perform and the time at which it is due. Furthermore, the task due time 366 (e.g., "7:30") is shown to include a visual indicator or reminder (e.g., is colored green, is colored red, etc.) such that user can visually see the task due time 366 and know if the task is due, overdue, or about to be due without knowing the actual time In some embodiments, each of the pieces of device data 360, the task type 364, and the task due time 366 may further be buttons such that if the user selects each, the workflow management application 120 navigates the user to the third page 368. In other embodiments, each of the pieces of device data 360, the task type 364, and the task due time 366 may be selectable such that if the user selects or clicks each, the user may be presented with a completed task data page. In this way, by selecting each of the pieces of device data 360, the task type 364, or the task due time 366 the user may input task data relating to when the task was completed, the staff that completed the task, etc.

Figure 8:
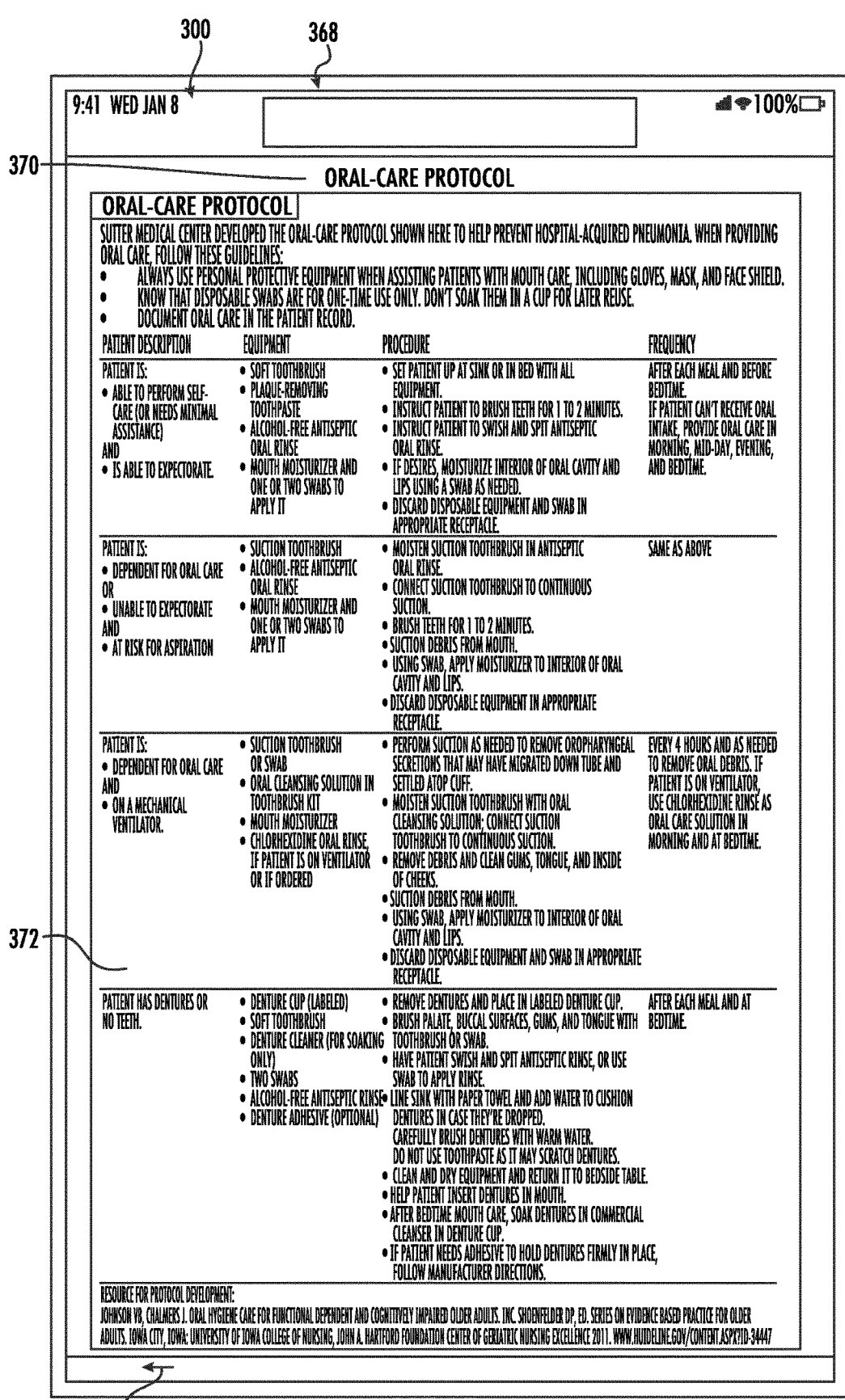

Referring now to FIG. 8, the user may be navigated to the third page 368 by selecting the protocol button 350. The third page 368 is structured to provide the user with data relating to the selected medical device and any tasks related to the selected medical device. As a result, the third page 368 includes the back button 325, a header 370, and a task description 372. The header 370 may provide an overview of the data that is being displayed in the task description 372, and the task description 372 may include the respective health care provider's protocols relating to the task or the device such as how the task is to be completed, best practices for completing the task, etc. In this way, the descriptions 372 may be received from the device database 189 and include data relating to the protocol the health care provider follows in using that device or performing the tasks associated with that device. Furthermore, the task description may be set by the healthcare provider by updating the description within the device database 189 at any time.

Figure 9:
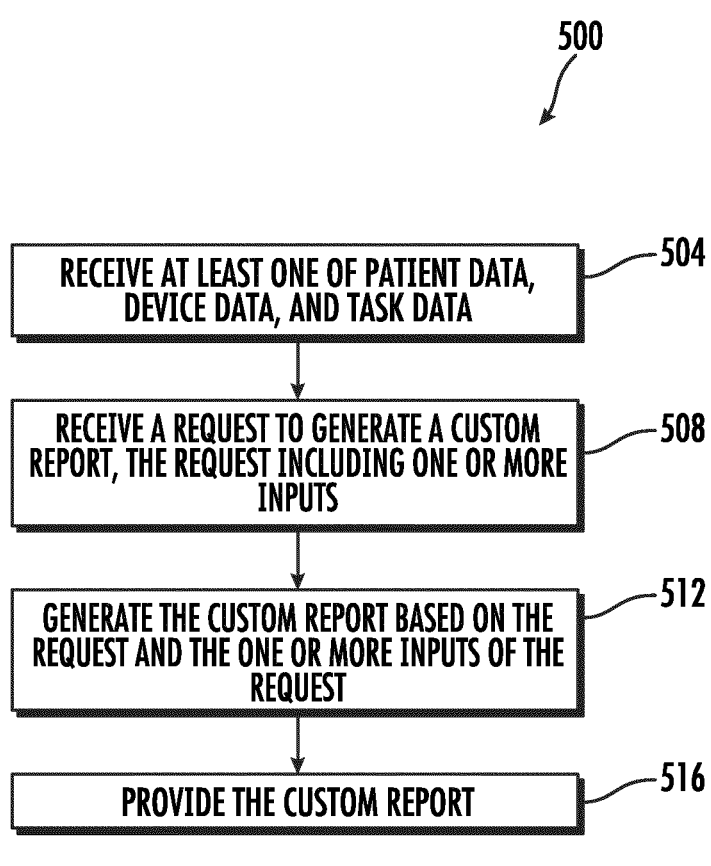
FIG. 9 is a flow diagram of a method of generating a custom report by the workflow management application of FIG. 2, according to an example embodiment.

Referring now to FIG. 9, a method 500 for processing data (or data) relating to the medical device task generation and management system 10 is shown, according to an example embodiment. Operations of the method 500 may be conducted by the medical device task generation and management system 10 (e.g., the analytics sub-circuit 192 of the workflow management application 120 of any of the server computing system 50, the one or more management computing devices 104, the one or more administrative staff computing devices 124, the one or more bedside staff computing devices 138, and/or the one or more personal staff computing devices 152). Through the steps of the method 500, the respective staff computing devices or the server computing system 50 process data and generate a custom report based on the data. The custom report may then be used to track analytics, statistics, etc.

As shown, the method 500 commences at step 504 in which one of the computing devices receives at least one of patient data, device data, staff data, and task data The staff data may relate to the patient data and include data relating to the specific staff member (e.g., staff name, employee number, patients under the staff members direct care, tasks completed by the staff member, number of tasks overdue, etc.). In some embodiments, the computing device may receive the patient data, device data, staff data, and task data from the health care provider computing device 174 (e.g., via one or more of the databases located therein) or the server computing system 50 where the data (data) may be stored (as related to step 232 of the method 200). In other embodiments, the patient data, device data, and task data may be received from an external source (e.g., a third party application, a user of the workflow management application 120, over the internet, etc.). Additionally, the data may be received as a set of data (e.g., a plurality of data) such that the user of the workflow management application 120 can glean useful data and patterns from the data. Further it should be understood that in some embodiments, all of the data types may be related in that one type of data (e.g., patient data) can be generated from another type of data (e.g., task data). For example, the tasks data may include data relating to the staff member who completed the task (e.g., staff data). In this way, the various types of data may all be associated with one another and one type of data may be used to generate another type of data.

Once the data has been received, the method 500 proceeds to a step 508 in which the computing device (e.g., the management computing device 104) may receive a request including one or more inputs that indicate what data is to be used to generate the custom report. In some embodiments step 508 may take place prior to step 504 (e.g., the management computing device 104 receives the request and then receives the data). In other embodiments, the computing device may receive the request and then request, acquire, and/or collect the necessary data. The request includes one or more inputs that indicate what data is to be used to generate the custom report and the type of report that is to be generated using the data (e.g., a graphical chart, an expense report, etc.). For example, the management computing device 104 may receive a request from the user of the workflow management application 120 with inputs relating to the number of tasks a specific unit (e.g., a predefined group of staff members) has completed over a specified period of time (e.g., the past day) as well as a specific type of custom report that the data is to be applied to. In some embodiment, each request may include a plurality of inputs indicating how what data is to be used to generate the custom report and the type of custom report itself.

By allowing the requesting party (i.e., the party that generated the request) to decide the data that will be used to generate the custom report, the workflow management application 120 allows the requesting party to better customize and decide the custom report they want returned. For example, a manager using the management computing device 104 can generate a request that relates to management (e.g., a report indicating the total staffing numbers used on a specific unit, a report identifying staff members that did not meet compliance, or a report with the total unit task statistics within the last month, etc.), and an administrative staff member using the administrative staff computing device 124 can generate a request that relates to administrative duties (e.g., a report indicating total number of device x that was used in the last month, a report indicating the total number of devices x used on task x, a report indicating the total number of device x, y, and z used in the last week, etc.). In some embodiments, the workflow management application 120 includes a set number of inputs for the report as well as report types. For example, the workflow management application 120 may include the data inputs of: staff member, room number, patient name or visitor ID, product identifier (e.g., serial number, model number, internal number, name, etc.), time or date, the task or protocol, the unit, the shift, a date range, a time range, tasks completed on time (e.g., within the due date and time due of the task), and tasks completed late (outside of the due date and time due of the task). These inputs may then be combined or processed to create the various data types that are used to generate the report. In some embodiments, the request may further include an option or button to receive a raw dataset. For example, the request may simply ask for the raw task data to be provided.

Once the request has been received, the method 500 proceeds to step 512 in which the workflow management application 120 generates the custom report based on data indicated by the inputs and the request itself. In some embodiments, the data must be refined or processed (i.e., the correct data indicated by the inputs must be identified) prior to the workflow management application 120 generating the custom report. Any processing or refining of the data may be performed by the analytics generation sub-circuit 192 or another data processing specific circuit. In some embodiments, data may be refined or processed by searching or determining the data that matches or is closest to matching the one or more requested inputs and then returning that data prior to being used to generate the report. Once the data indicated by the inputs has been acquired, the workflow management application 120 generates the custom report based on the data and the report type. As described herein, the workflow management application 120 may include one or more preset types of reports (e.g., compliance chart, pie chart, line chart, etc.) that are specifically indicated by the request itself.

Once the custom report has been generated, the method 500 proceeds to step 516 in which the custom report is provided or transmitted based on the request. In one embodiment, each request may further include a destination for the custom report and the custom report may be provided to that destination. For example, the user interface (e.g., the user interface 300) may receive the request and then provide the destination as the user interface for further representation (as will be discussed further herein) as one or more charts displayed to the user via the user interface 300. As a result, the user interface may receive the custom report and then represent the data to the user. In other embodiments, the requesting party may specify a location within the staff computing device (e.g., the manager computing device 104) and the custom report may be provided as varying file types to that location. In even other embodiments, the requesting party may specify a location over the network or via email. As such, the workflow management application 120 may provide the custom report to the respective network interface circuit (e.g., the network interface circuit 110) which may provide the custom report to the requesting party via the network 170.

Referring now to FIGS. 11-17, a fourth page 378 and a fifth page 396 of the user interface 300 that may be displayed (e.g., via the display of the respective input/output circuit) to the user (e.g., during, before, and after the method 500) are shown, according to an example embodiment. The fourth page 378 and the fifth page 396 are provided to the user to allow the user to generate one or more sets of custom reports and view the custom reports in a chart or other form of representation. In use, the fourth page 378 (FIGS. 11-13) allows the user of the workflow management application 120 to decide and choose the one or more inputs indicating the data that will be used to generate the custom report, and the fifth page 398 (FIGS. 14-17) displays the custom report a graphical fashion. To access the fourth page 378 from the first page 302, the user can select or press the report button 312 (see FIG. 10). Once selected, the report button 312 will generate/navigate the user to the fourth page 378.

The fourth page 378 allows the user to set the one or more inputs specifying the data for the custom report and therefore includes the home button 324, an input drop down box 382, multiple data input check boxes 388, and a generate report button 392. The input drop down box 382 is a selectable or clickable box that when selected drops down one or more data input options 384. By selecting or clicking the data input options 384, the user of the workflow management application 120 can set the data inputs relating to the data that will be used to generate (see the method 500) the custom report. In some embodiments, only a single data input option 384 is selectable at one time. In other embodiments, multiple data input options 384 can be selected at one time. In the embodiment shown, the input drop down box 382 includes four data input options 384 each relating to a device and task type: "Turn Protocol," "Oral Care Protocol," "Product Usage," and "Overall Compliance." In some embodiments, the input drop down box 382 further includes an "insert type here" option 384 in which the user of the workflow management application 120 can input one or more custom inputs.

The multiple data input check boxes 388 further define the input relating to the data and are configured to be checked or selected by a user to add one or more inputs. For example, when checked (see FIG. 13), the check boxes 388 define additional inputs relating to the data that is to be used to generate the custom report. In the embodiment shown, there are four check boxes 388, each relating to an additional input: "Time," "Date," Room ID," and "Clinician ID." By selecting one or more data input options 384 via the input drop down box 382 and then "checking" one or more data input check boxes 388, the user of the workflow management application 120 can better define the input relating to the data that is be used to generate the custom report and decide what data the custom report includes. To send the request (in relation to step 508), the user can select or click the generate report button 392. The generate report button 392, when selected, will cause the workflow management application 120 to generate a report request including the one or more inputs that the user has selected. Additionally, once the generate report button 392 is selected, the custom report may be provided to the fifth page 396 and used to generate one or more charts 404.

Figures 14, 15:
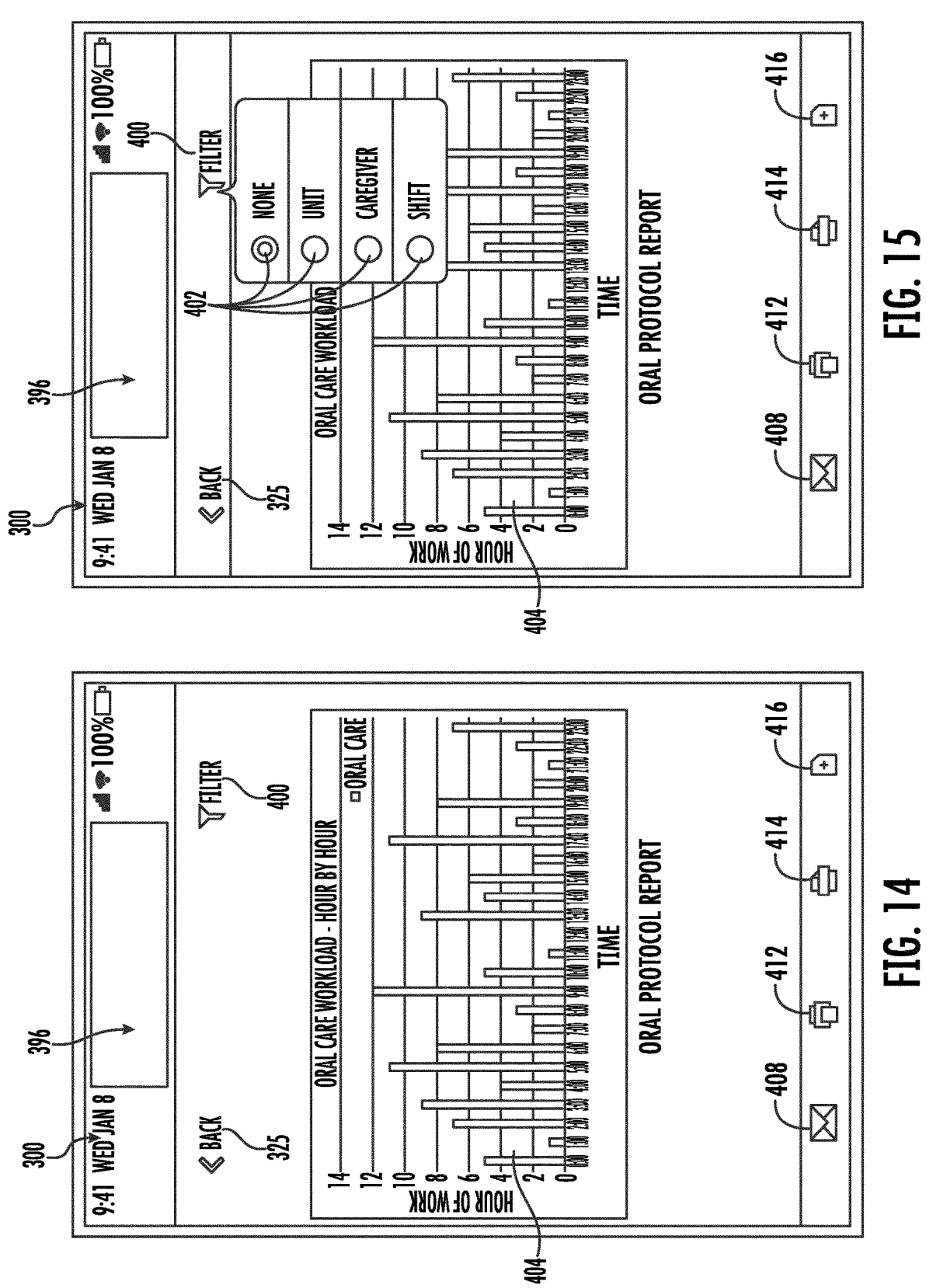
Figure 17:
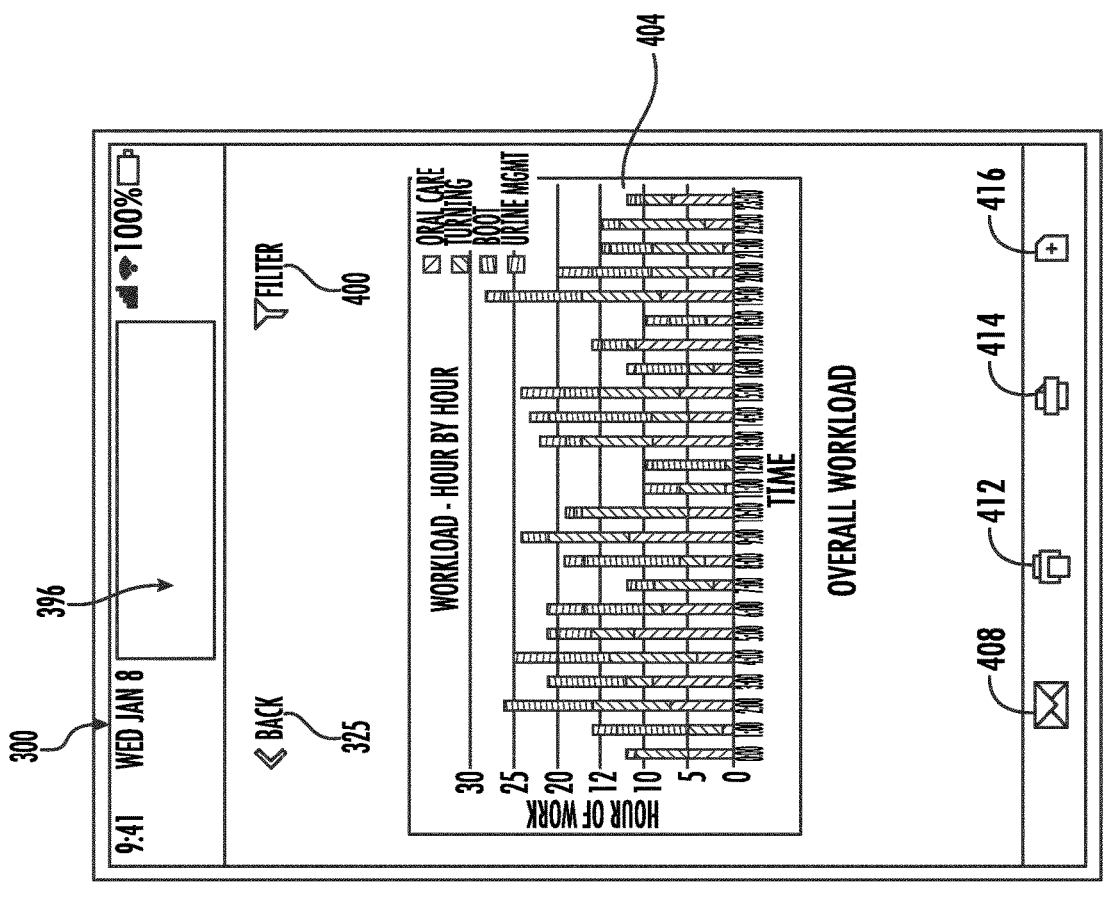
Figure 16:
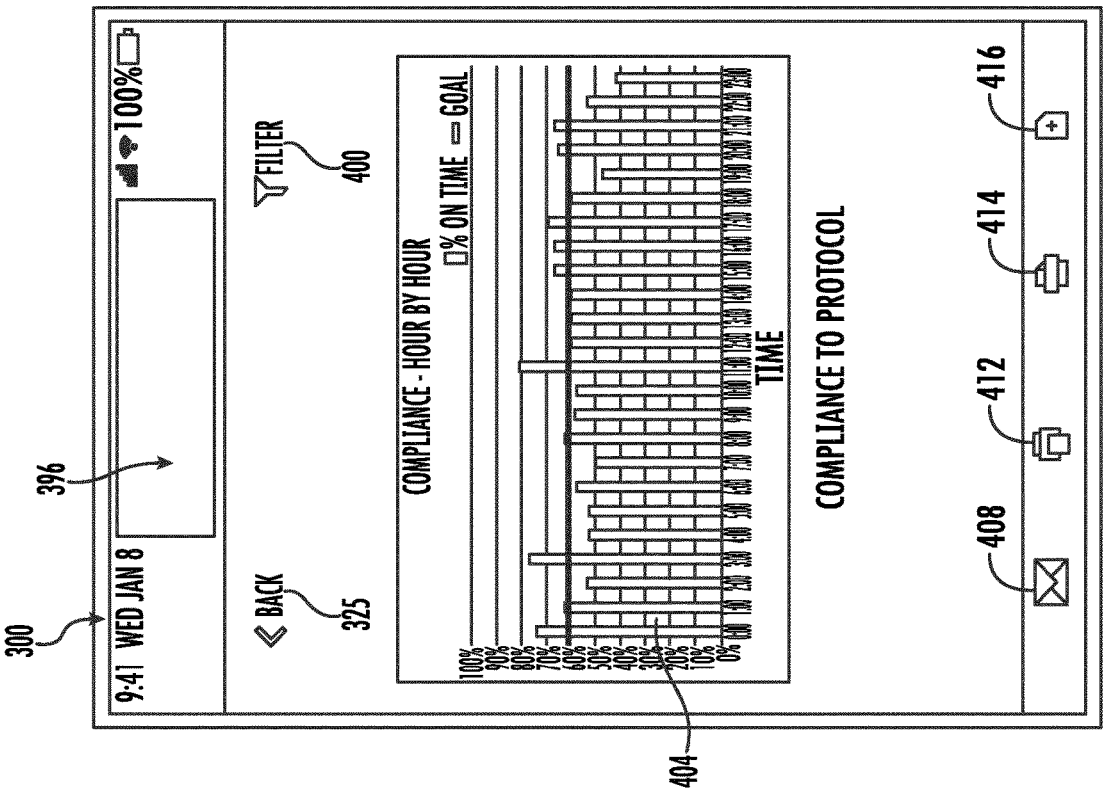

The fifth page 396 of the user interface 300 is generated and displayed to the user to provide a graphical display of the custom report. As such, the fifth page 396 may include the back button 325, a filter button 400, a graph or chart 404, an email button 408, a print button 412, an export data button 414, and a generate new report button 416. The chart 404 includes the custom report based on the data input(s). In FIG. 14, the data inputs were the task "Oral Care Protocol," based on the time (X-axis) and the number of tasks completed (Y-Axis). The chart 404 may take many different forms including a bar chart, a line chart, a histogram, a pie chart, a Cartesian graph, or other types which all may be selectable via the fourth page 378 (not shown). Additionally, the user may be able to change the data displayed on the chart 404 by adding or removing one or more filters via the filter button 400. The filter button 400, when selected, may drop down one or more selectable filter options 402 that allow the data within the chart 404 to be further refined. In the example shown in FIG. 15, the filter options include "None," "Unit," "Caregiver," and "Shift." Therefore, the user may be able to filter the data by selecting one or more of the filter options to filter specific data of the data. In one example, a nurse manager may filter the data using the filter button 400 and the filter options 402 to see the statistics of a specific caregiver for the oral care task over the past four weeks. This allows the nurse manager to evaluate the specific caregivers performance.

The email button 408, the print button 412, and the export data button 414 are selectable buttons that when selected allow the outputting or providing of the chart 404 or the data of the chart to the user or others. For example, by pressing the email button 408, a third party email application may be launched that includes one or more snapshots, images, .pdf, or other files types of the chart 404. In this way, the user may then enter an email address and send the charts 404 for various reasons. In one example, a purchasing staff member may be using the fourth page 378 and the fifth page 396 to determine stock of one or more devices. The chart 404 may then indicate that an unusually large number of one medical device was used on Tuesday and that the hospital will be out of the device by Friday. The staff member may then email the chart 404 and accompanying data to their boss to justify purchasing more of the device, early. This saves the staff member from having to get the raw data and generate a chart that will be sent in the email. Similarly, the print button 412 may be selected and bring up a third party or computer specific printing application. From there, the user of the workflow management application 120 may decide which pages or charts 404 to print. Similarly, the export data button 414 may output the data within the chart 404 as a specified file type (e.g., .raw, .csv, etc.) and to a specific location on the respective computing device or to another computing device.

Still referring to FIGS. 14-17, the generate new report button 416 is a selectable button that when clicked returns the user to the fourth page 378 to generate additional reports. In this way, the generate new report button 416 allows the user to return to the fourth page 378 to change one or more data inputs and to change the data being shown in the chart 404. For example, the user may realize that they entered the wrong date range via the fourth page 378 and therefore want to change the date range. The user may select the generate new report button 416, select or indicate the correct date range, and return to the fifth page 396 to view the updated (based on new data) chart 404. For example, the user may generate a report on the chart 404 that displays compliance to protocol (time of day vs % of tasks completed on time) or a report that shows the overall share of workload of each task (see FIG. 17).

Figure 18:
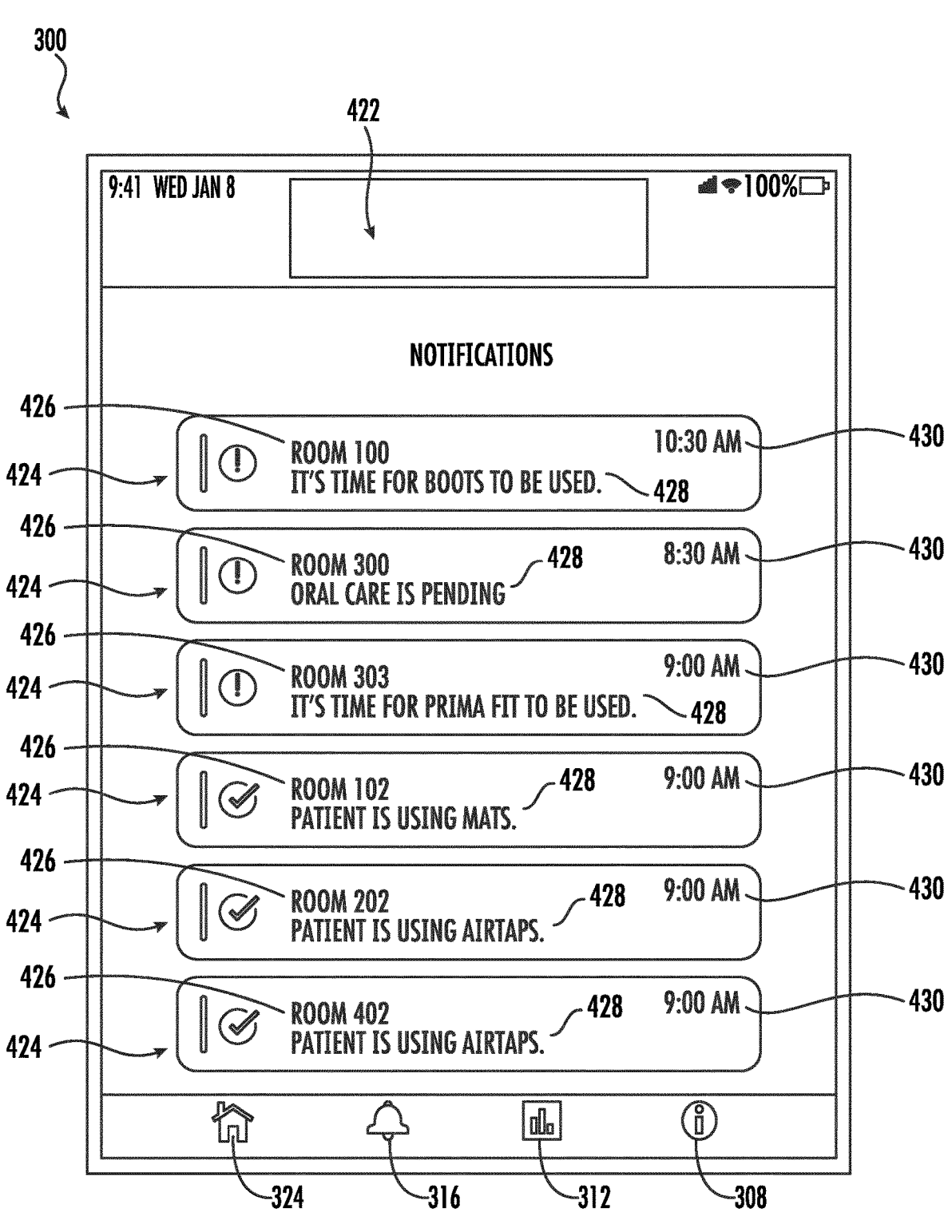
FIGS. 18-24 are additional illustrations of the user interface of FIG. 4 usable in connection with the method of FIG. 3 and of FIG. 4.

Referring now to FIG. 18, a sixth page 422 of the user interface 300 is shown, according to an example embodiment. The sixth page 422 may be accessed via any of the other pages of the user interface 300 by selecting the notification button 316 and is structured to provide the user up to date alerts or notifications that require or will require the user's attention. When the notification button 316 is pressed or selected, the sixth page 422 may be generated and the user may be navigated to the sixth page 422 such that they can see any notifications or alerts via the sixth page 422. Similar to the other pages of the user interface 300, the sixth page 422 includes the profile button 308, the report button 312, the notification button 316, and the home button 324, which together allow the user to navigate to the other pages of the user interface 300.

The sixth page 422 further includes multiple visual notifications or alerts 424 that are specific to the user. Each visual notification or alert 424 may be generated as described herein with respect to method 200 and provides the user of the workflow management application 120 a visual listing of the task, the task due time, and the patient for which the task is associated with. Therefore, each visual notification 424 includes a patient identifier 426 that identifies the associated patient, a task type or device type field 428 that identifies the task or device associated with the task, and a task due time field 430 that identifies when the task is due. The visual notifications 424 may then be listed and displayed on the sixth page 422 such that the user can see the visual notifications 424 and take action on the respective tasks. Furthermore, each of the visual notifications 424 may be include a visual indicator (e.g. be in a specific color (e.g., green, yellow, red, grey, and white)) such that the color of the visual notification 424 provides the user an idea if the task is due, overdue, not yet due, etc. For example, in the example shown in FIG. 18, the first visual notification is yellow such that the user of the workflow management application 120 knows that room 100 has a task that is due.

In some embodiments, each of the visual notifications 424 may further be clickable or selectable (e.g., a button) such that if the user presses the visual notification one or more actions happen. In some embodiments, if the user presses the visual notification 424 they are navigated to the second page 320 of the specific patient so they can handle the one or more task associated with the patient. In other embodiments, if the user presses the visual notification 424 they are navigated to a task completion page (as will be discussed further herein) so they can mark the task as completed and enter various details surrounding the completion of the task.

Figure 20:
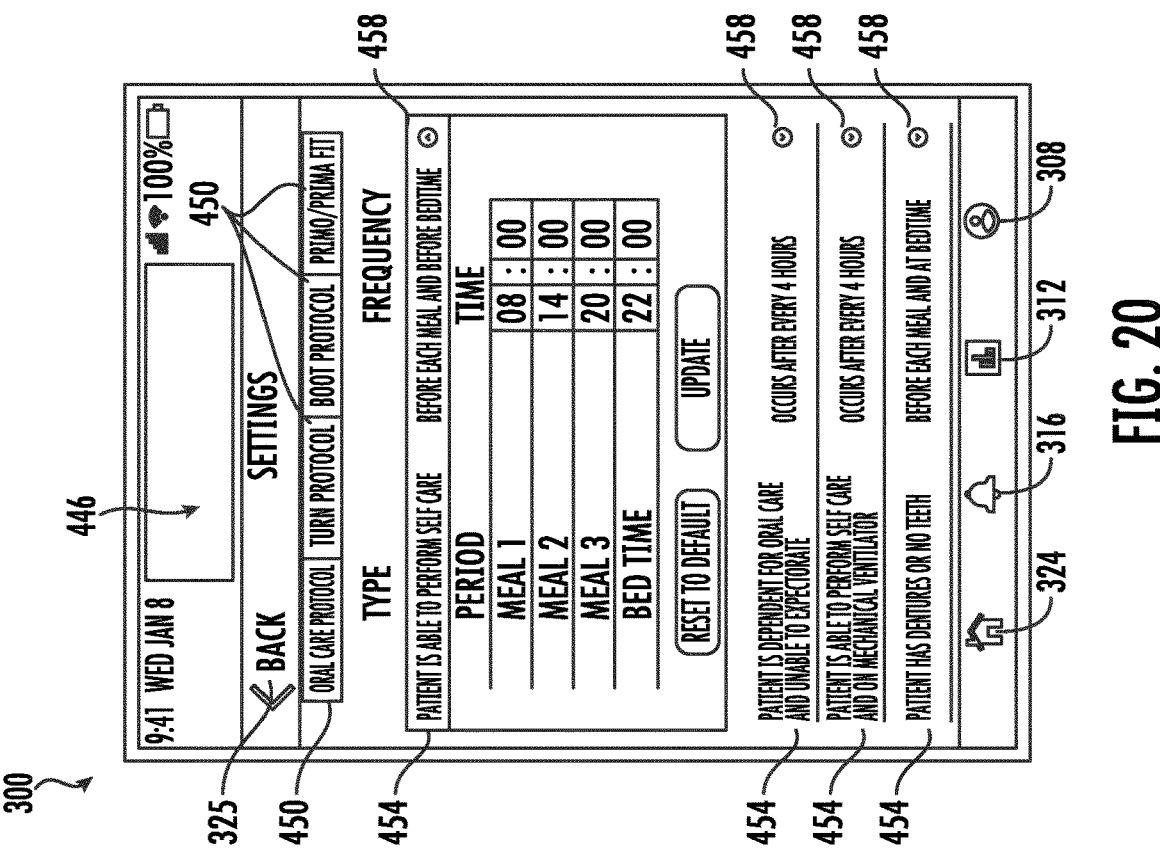
Figure 19:
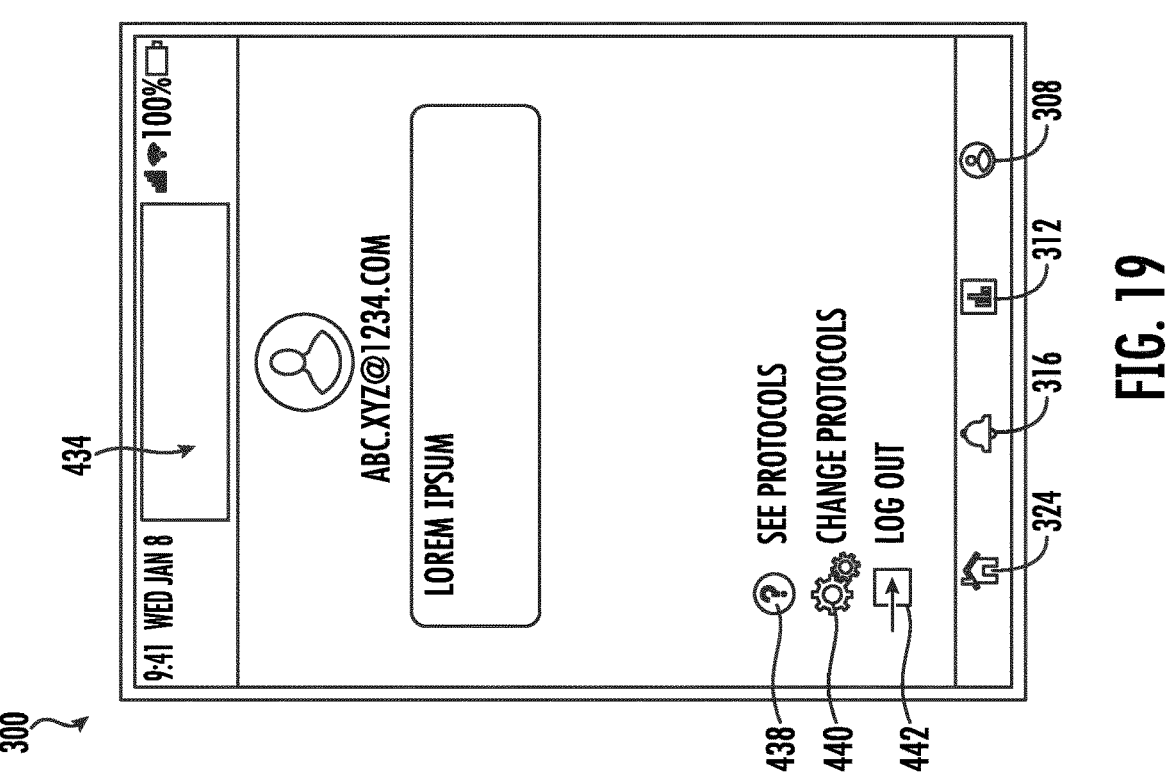

Referring now to FIGS. 19-20, a seventh page 434 and an eighth page 446 of the user interface 300 are shown, according to an example embodiment. The seventh page 434 may be accessed via any of the previous pages of the user interface 300 by selecting or clicking the profile button 308. Furthermore, the seventh page 434 is structured to provide the user with specific user settings and preferences such that the user can edit their personal preferences or settings. Similar to the other pages of the user interface 300, the seventh page 434 includes the profile button 308, the report button 312, the notifications button 316, and the home button 324.

In use, the user may navigate to the seventh page via the profile button 308 to change one or more protocols or preferences of the user. As described herein, the user may be required to login and be authenticated prior to accessing the pages of the user interface 300 and therefore may have a specific user profile. The user profile may be setup using credentials of the user (e.g., a username and password of the user) and therefore may allow the user to set one or more preferences that are specific to the user. Furthermore, certain users with additional authorization (e.g., a manager, a doctor, etc.) may also be able to edit task protocols of the workflow management application 120 such that users with additional authorization may be able to customize the many tasks that are generated and the due date/due time of each task. Therefore, the seventh page also includes a protocols button 438 through which the user can see the one or more protocols of the specific group of staff members, a change protocols button 440 through which certain users (with authorization) can change the protocols for the specific group of staff members, and a logout button 442 through which the user can logout of the workflow management application 120. In some embodiments, only users with the correct authorization will see the change protocols button 440 displayed on the seventh page 434. In other embodiments, all users will see the change protocols button 440 displayed on the seventh page 434, but only users with the correct authorization will be able to change the task protocols.

When the user selects or clicks the change protocols button 440, the user is then navigated to the eighth page 446 through which the user can change one or more task protocols. As described herein, the "task protocols" refer to each of the tasks that are automatically generated for a specific device and the task due date and due time for each task which can be either decided solely by the healthcare provider or by the healthcare provider in combination with the user. For example, a healthcare provider may require that a catheter is cleaned every four hours, but certain managers (and users) may prefer that every catheter on their unit is cleaned every two hours. In this way, the healthcare provider may have a healthcare provider specific task protocol and the unit may have a unit specific task protocol. Once the user has accessed the eighth page 446, the user may change multiple task protocols by selecting and setting one or more medical device settings 450. The medical device settings 450 relate to the settings of the multiple healthcare devices that the tasks may generated for and therefore includes one or more task settings 454, and one or more due date and due time settings 458. For example, the user can add or remove one or medical devices via the medical device settings 450. Then, using the task settings 454 the user can add or remove one or more tasks for a specific device. For example, if the user wants to add an additional task for a specific device or remove an extra task for a specific device they may do so via the task settings 454. Furthermore, the user may also change the due date and due time settings 458 which may be frequency specific or date specific as discussed herein.

In some embodiments, any user may be able to add one or more devices or tasks but only an authorized user may be able to remove one or more devices or tasks. In even other embodiments only authorized users may be able to remove or add one or more devices or tasks via the medical device settings 450 and the task settings 454. In even other embodiments, only authorized users may be able to add or more remove one or more devices but any user can add a task via the medical device settings 450 and the task settings 454. In this way, the settings can be configured to the preferences of the specific healthcare provider.

Figure 21:
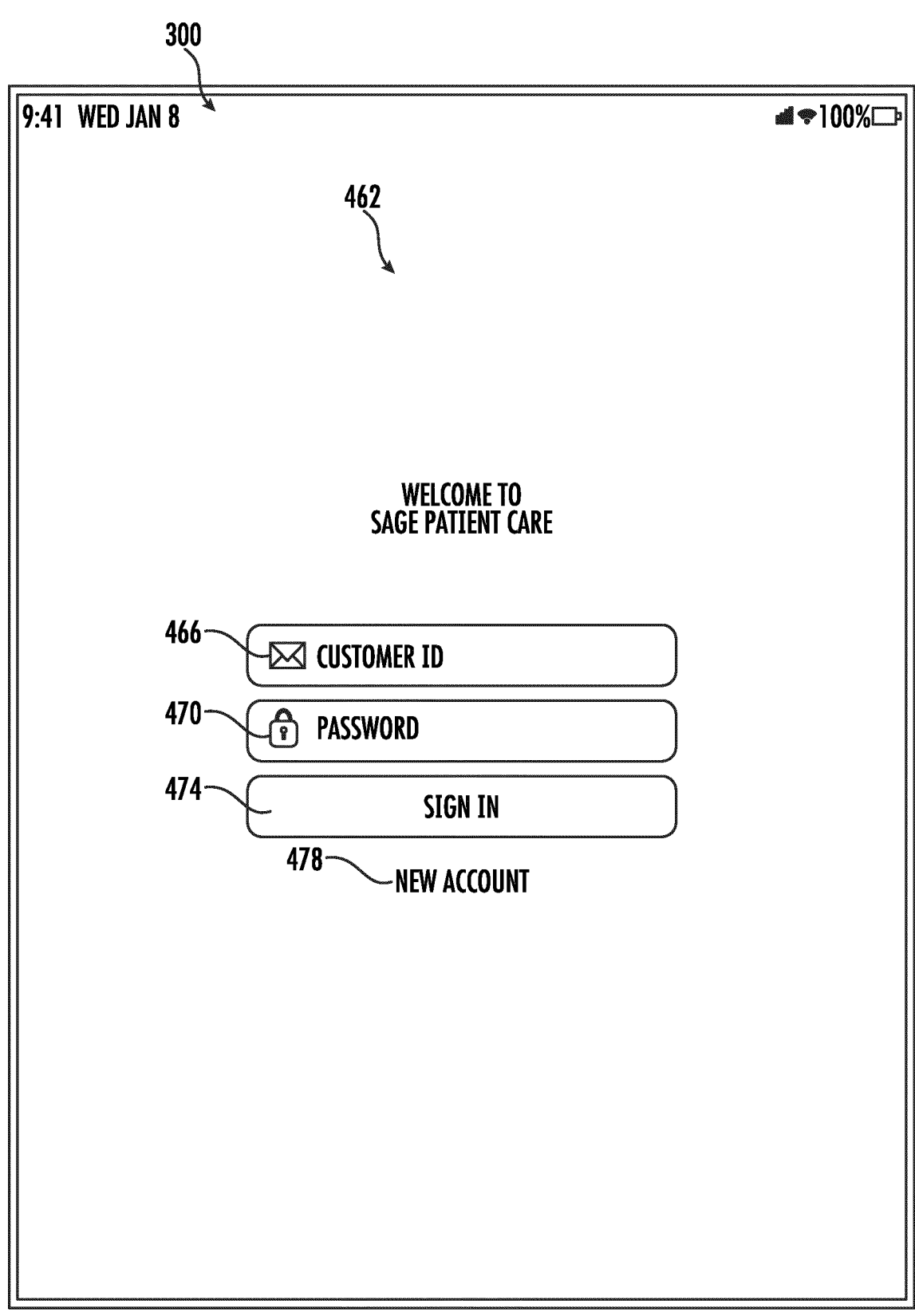

Referring now to FIG. 21, a login page 462 of the user interface 300 is shown according to an example embodiment. If the user were to select the logout button 442 or was accessing the workflow management application 120 for the first time in a session, the login page 462 would be displayed to the user. The login page is structured to prevent unauthenticated users from accessing patient data, task data, device data, and any other data of the user interface 300 and to also receive authentication data from the user to authenticate the user and allow them to access the other pages of the user interface 300. In some embodiments, if the user of the workflow management application 120 does not have an account or authentication data they cannot access the other pages of user interface 300 and will be prevented from doing so by the login page. 462 In other embodiments, new users may have to first make an account before being able to access any other of the pages of the user interface 300. In even other embodiments, to make an account, new users may have to be added into the employee database 188 and have a healthcare provider username and password.

To authenticate the user, the login page 462 includes a username field 466 into which the user can enter their username, a password field 470 into which the user can enter their password, a sign in button 474 that the user can select to sign in, and a create new account button 478 that the user can select to create a new account. As described herein, the username field 466 and the password field 470 are two text fields into which the login page 462 may require the user to enter their corresponding username and password to authenticate the user. In other embodiments, other forms of authentication may be required by the login page 462. For example, dual authentication may be required (e.g., a one-time code from an email, a one-time code from a text message, biometric data, a PIN number, etc.) in addition to the username and password. Once the user has entered their authentication data into the username field 466 and the password field 470, the user may click the sign in button 474. If the user is authenticated via their authentication data, the user may then be directed to their home page. If the user is not authenticated via their authentication data, a notification may be displayed via the login page 462 that notifies the user their authentication data was incorrect. In other embodiments, un-authenticated users may be able to access certain pages (e.g., the first page 302, a dashboard, etc.) but may be required to login and be authenticated to see any patient specific or account specific data.

If the user does not already have a username, a password, and dual authentication data (i.e., it is their first time using the workflow management application 120), they may select the create new account button 478 and be directed to a new account creation page. In some embodiments, the user will only be able to create a new account if they have a healthcare provider specific account (e.g., if they are added to the employee database 188, if they have a healthcare provider specific email, etc.).

Figure 22:
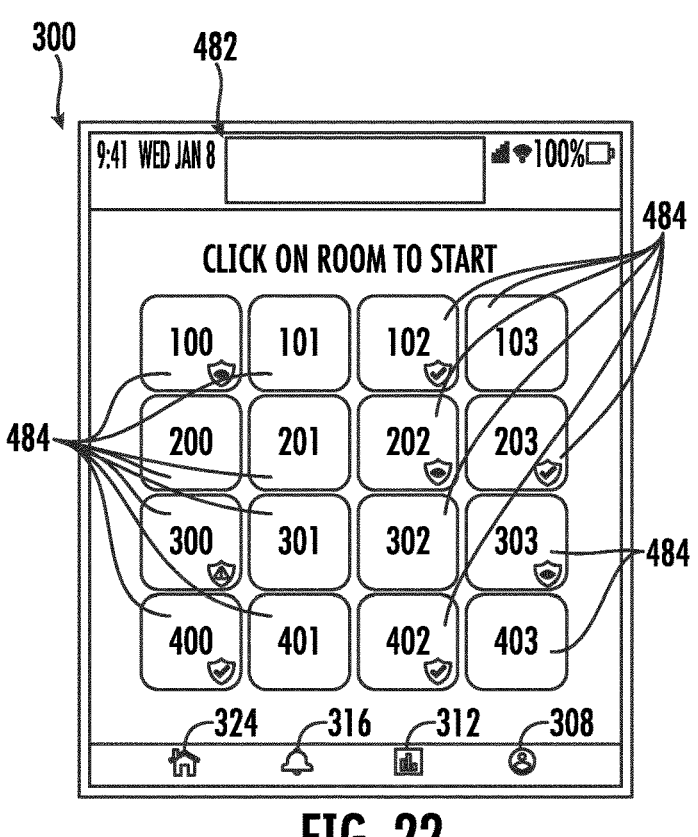

Referring now to FIG. 22, a ninth page 482 that may be displayed in place of or in addition to the first page 302 on the user interface 300 is shown, according to an example embodiment. Similar to the first page 302, the ninth page 482 is structured to provide an overview of all the patients in a specific unit or under the care of a specific employee (e.g., the user) as well as to allow the user to then navigate to the patient specific pages (e.g., the second page 320). As a result, the ninth page 482 includes the profile button 308, the report button 312, the notifications button 316, and the home button 324 which allow the user to navigate to one or more pages of the user interface 300 as described herein. Further, the ninth page 482 includes one or more patient buttons 484 (depending on the number of patients) that may be similar to the patient buttons 318. Each patient button 484, when selected, navigates the user to the patient specific page (e.g., the second page 320) of the patient that the patient button 484 identifies. For example, if the user were to select the number "100" patient button 484, the user would be navigated to the second page 320 specific to the patient in room number 100. Furthermore, each patient button 484 includes a visual indication of the status any tasks that may be associated with the respective patient. Unlike the patient buttons 318, each patient button 484 is not filled entirely with a color (e.g., red, green, yellow, white) to provide an indication of the status of the tasks but rather includes a small emblem in the bottom right corner that provides a visual indication of the status of any tasks associated with the respective patient. In the example shown in FIG. 22, the emblem is a shield that includes a picture of the device for which the task is due and that is filled with a color visually indicating the status of any task. In rooms where there is no patient, the patient button 484 does not include an emblem. In rooms where there is a patient but no tasks due or coming due, the emblem includes a grey color and is a check mark.

Figure 23:
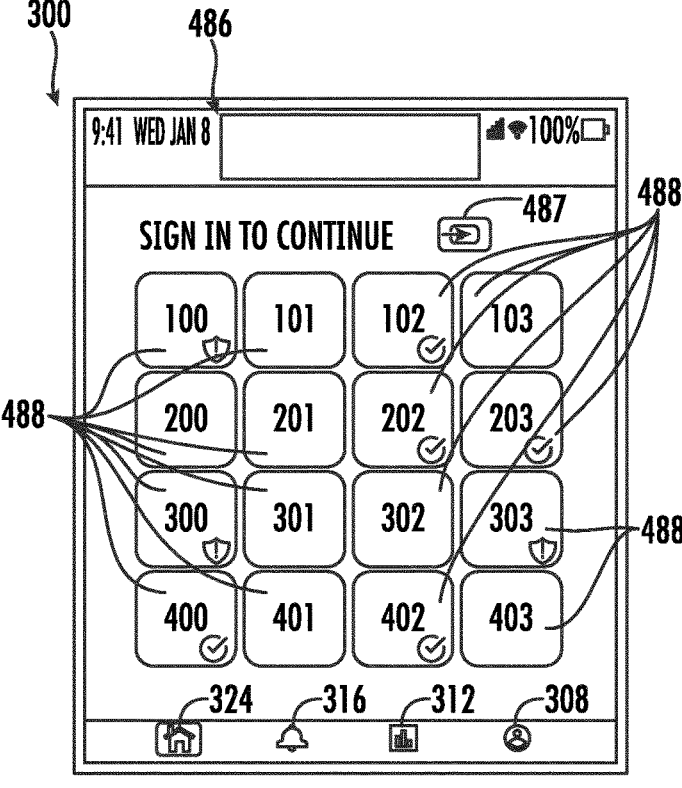

Referring now to FIG. 23, a tenth page 486 that may be displayed in place of or in addition to the first page 302 and/or the ninth page 482 on the user interface 300 is shown, according to an example embodiment. Similar to the first page 302 and the ninth page 482, the tenth page 486 is structured to provide an overview of all the patients in a specific unit or under the care of a specific employee (e.g., the user) as well as to allow the user to then navigate to the patient specific pages (e.g., the second page 320). As a result, the tenth page 486 includes the profile button 308, the report button 312, the notifications button 316, and the home button 324 which allow the user to navigate to one or more pages of the user interface 300 as described herein. Additionally, the tenth page 486 is a page that may be accessed when the user is not yet authenticated (e.g., logged in) and therefore includes a sign in button 487. In use, the user may be able to access the tenth page 486, prior to being authenticated, to see a visual overview of the status of the tasks associated with the patients under the care of the user. In this way, the user does not need to take the time to login, can see an overview of the status of the tasks, and then take action on those tasks. If however the user needs to see patient specific data or would like to navigate to other pages of the user interface 300, the user can press the sign in button 487 and be navigated to the login page 462. In some embodiments, if the user is not authenticated and presses other buttons on the tenth page 486, the user will still be navigated to the login page 462 until the user is authenticated.

Furthermore, the tenth page 486 includes one or more patient buttons 488 (depending on the number of patients) that may be similar to the patient buttons 318 and the patient buttons 484. Each patient button 488, when selected, navigates the user to the patient specific page (e.g., the second page 320) of the patient that the patient button 488 identifies. Furthermore, each patient button 488 includes a visual indication of the status any tasks that may be associated with the respective patient. To provide a visual indication, each patient button 484 is filled entirely with a color (e.g., red, green, yellow, white) to provide an indication of the status of the tasks and also includes a small emblem in the bottom right corner that provides a visual indication of the status of any tasks associated with the respective patient. In the example shown in FIG. 23, the emblem is a shield that includes a picture of the device for which the task is due and that is filled with the color visually indicating the status of any task. In rooms where there is no patient, the patient button 488 does not include an emblem. In rooms where there is a patient but no tasks due or coming due, the patient button 488 is a colored in grey and includes a black check mark emblem.

Figure 24:
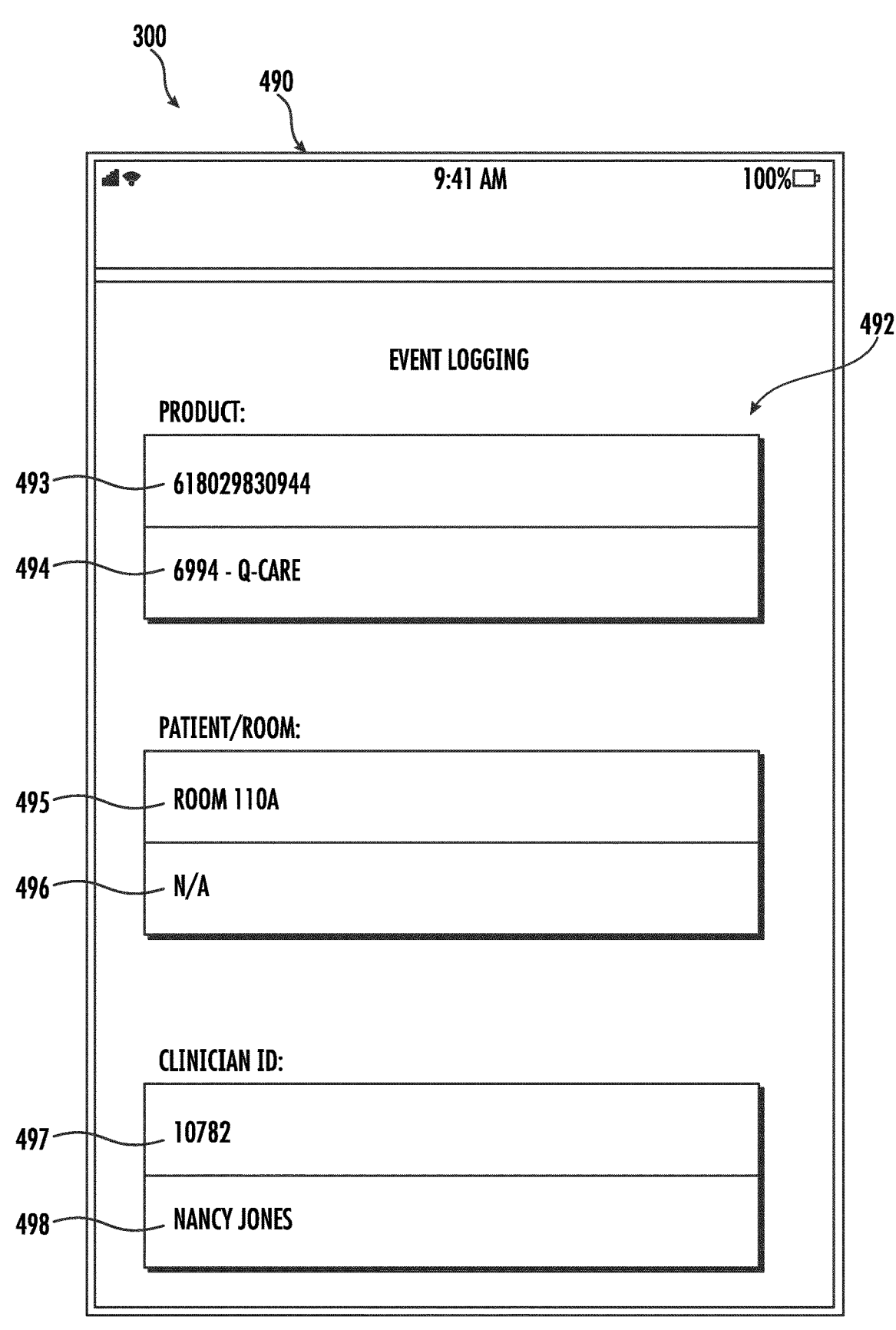

Referring now to FIG. 24, an eleventh page 490 of the user interface 300 is shown, according to an example embodiment. In situations where the user has just completed a task, they may navigate to the eleventh page 490 through one or more actions to mark the task as completed. In some embodiments, the user is navigated to the eleventh page 490 by selecting the visual notifications 424 of the sixth page 422. In other embodiments, the user is navigated to the eleventh page 490 by selecting one or more of the device representations, the patient representation 336, the device data 360, the task type 364, or the task due time 366 of the second page 320. The eleventh page 490 is structured to allow the user to input (or have transferred over) one or more details relating to a completed task and to mark the task as complete. To do so, the eleventh page 490 includes a completed task details box 492 through which the user inputs the details of the completed task.

The completed task details box 492 provides the user a place to select and enter one or more details regarding the task, and therefore includes the device data section 493 into which the user enters the associated device data, the task data/type section 494 into which the user enters the task data, the patient room data section 495 into which the user enters the patient room data, the patient secondary data section 496 into which the user enters any secondary patient data, the staff member ID section 497 into which the user enters the staff member ID number who completed the task, and the staff member secondary data section 498 into which the user enters any secondary staff member data. In operation, each of the sections (e.g., 493-498) may be clickable or selectable such that when a user clicks the sections the user can input data or text into each. In this way, the user may navigate to the eleventh page 490 to indicate that a task is completed and provide the various data relating to the task into each of the sections. In regard to time completed, the workflow management application 120 may use a clock of the computing system to gather the time completed data. In some embodiments, if the user selects a specific tasks (e.g., the visual notifications 424 of the sixth page 422) the workflow management application 120 may automatically fill out the one or more sections for which it has the data. For example and referring to FIG. 18, if the user were to select the first visual notification 424, the workflow management application 120 may input "Room 100" into the patient room data section 495. The user may then have to input data into/fill out the rest of the sections for which the workflow management application 120 does not have data. In other embodiments, the workflow management application 120 may fill out the remaining sections using data from the one or more databases (e.g., the employee database 188, the patient database 184, the device database 189, or the server database 74) or the respective memory (e.g., the memory 146). To then submit the data that has been entered into the sections, the user may exit the eleventh page 490 or the eleventh page 490 may include a complete task button (not shown). In some embodiments, all of the sections must be filled out before the task can be marked as completed. In other embodiments, all of the sections are not required to be filled out before the task can be marked as completed.

Figures 10, 11, 12, 13:
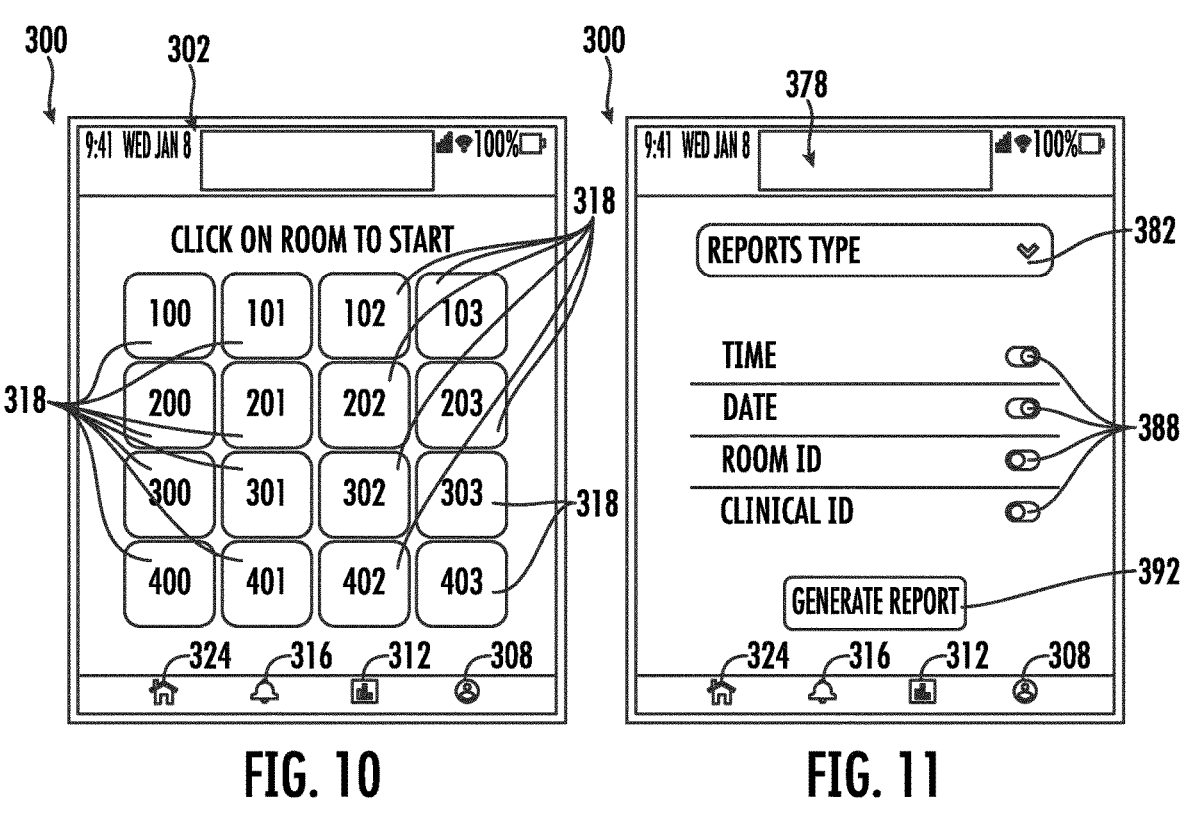
FIGS. 10-17 are additional illustrations of the user interface of FIG. 4 usable in connection with the method of FIG. 4.

Referring now to FIG. 12, a method 600 for updating an EMR of a patient related to the medical device task generation and management system 10 is shown, according to an example embodiment. Operations of the method 600 may be conducted by the medical device task generation and management system 10 (e.g., the third party integration subcircuit 194 of the workflow management application 120 of any of the server computing system 50, the one or more management computing devices 104, the one or more administrative staff computing devices 124, the one or more bedside staff computing devices 138, and/or the one or more personal staff computing devices 152). Through the steps of the method 600, the respective staff computing devices or the server computing system 50, receive or use the stored patient data within the workflow management application 120 to update the electronic medical record of a patient. As the EMR of a patient is typically an encrypted, protected, and regulated record, the workflow management application 120 must take one or more steps to add the patient data to the EMR.

The method 600 commences at step 604 in which the one of the computing devices receives patient data. In even other embodiments, the computing device may receive device data, task data, and staff data. In some embodiments, the computing device may receive the patient data from the health care provider computing device 174 (e.g., one or more of the databases located therein) or the server computing system 50 where the data (data) may be stored (as related to step 232 of the method 200). In other embodiments, the patient data may be received from an external source (e.g., a third party application, a user of the workflow management application 120, over the internet, etc.). Additionally, the patient data may be received as a set of data (e.g., a plurality of data) such that the user of the workflow management application 120 can glean useful data and patterns from the data.

Once the patient data has been received, the method 600 proceeds to step 608 at which a request to add the patient data to an electronic medical record of the patient is received. In some embodiments, step 608 takes place before step 604 (i.e., the request is received before the data is received). In other embodiments, step 608 may be skipped and the computing device may consistently update (e.g., at a predetermined interval) the EMR of the patient. For example, as compared to receiving a request, the computing device/the workflow management application 120 may determine that a predetermined interval of time has pass and generate an internal request to update the EMR of the patient. In other embodiments, whenever the patient profile is updated or generated (see method 200), the workflow management application 120 may generate an internal request to update the EMR of the patient. The request may include one or more of an EMR destination, a type of data required, etc. For example, the request may indicate that the workflow management application 120 is to upload the data to the EMR database 186 or that the workflow management application 120 is to provide the data to a third party application (e.g., Redox®) to upload the data to the EMR database 186 (or another EMR database). In other embodiments and prior to sending the data, the request may indicate that the data must be encrypted using a specific type of encryption.

Once the request has been received (or internally generated), the method 600 proceeds to a step 612 at which the computing device and the workflow management application 120 determine if the patient data (or the other data discussed above) need to processed prior to being provided. In one example and based on HIPAA, the workflow management application 120 may determine that the data needs to be encrypted prior to being provided. In other embodiments, the data may need to be processed into a specific format or input before being provided to the EMR of the patient. For example, the Redox® API may indicate that all data needs a timestamp in central standard time (CST) and not local time. The workflow management application 120 may determine that the patient data (or other data) includes a local time stamp (in one example, eastern time (EST)) and that the data must be processed to update each time stamp. In another example, the EMR database 186 may require all data to be compressed prior to being received and input into the EMR database 186. The workflow management application 120 may determine that the patient data is not compressed and that the patient data needs to compressed (processed) prior to providing the data If the (patient) data is determined to require processing, the method 600 may proceed to a step 616 at which the patient data is processed. The patient data may be processed in a variety of ways as described herein including being encrypted or being modified. In some embodiments, the data may be processed using one or more algorithms and by one or more specialized data processing circuits (e.g., the ana- lytics generation sub-circuit 192). If it is determined that the data does not require processing or after the data is pro- cessed, the method 600 proceeds to step 620 at which the (processed) data is provided to at least one of an electronic medical records database (e.g., the EMR database 186) or a third party application that is configured to interface with the EMR database (or another EMR database). For example, the workflow management application 120 may interface with a third party application (e.g., Redox®) to upload the patient data to the EMR of the patient. In other embodiments, the workflow management application 120 may interface with a third party application that includes the EMR database the health care provider uses to update the EMR of the patient. In this way, the workflow management application 120 may selectively update the EMR of the patient therefore integrat- ing the device data intake, task generation, and EMR all into one application.

The embodiments described herein have been described with reference to drawings. The drawings illustrate certain details of specific embodiments that implement the systems, methods and programs described herein. However, describ- ing the embodiments with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., inte- grated circuits (IC), discrete circuits, system on a chip (SOC) circuits), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexers, registers, capacitors, inductors, diodes, wiring, and so on.

The "circuit" may also include one or more processors communicatively coupled to one or more memory or memory devices. In this regard, the one or more processors may execute instructions stored in the memory or may execute instructions otherwise accessible to the one or more processors. In some embodiments, the one or more proces- sors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alter- natively or additionally, the one or more processors may be structured to perform or otherwise execute certain opera- tions independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits (ASICs), field pro- grammable gate arrays (FPGAs), digital signal processors (DSPs), or other suitable electronic data processing compo- nents structured to execute instructions provided by memory. The one or more processors may take the form of a single core processor, multi-core processor (e.g., a dual core processor, triple core processor, quad core processor), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system) or remotely (e.g., as part of a remote server such as a cloud based server). To that end, a "circuit" as described herein may include components that are distributed across one or more locations.

An exemplary system for implementing the overall sys- tem or portions of the embodiments might include a general purpose computing devices in the form of computers, including a processing unit, a system memory, and a system bus that couples various system components including the system memory to the processing unit. Each memory device may include non-transient volatile storage media, non-vola- tile storage media, non-transitory storage media (e.g., one or more volatile and/or non-volatile memories), etc. In some embodiments, the non-volatile media may take the form of ROM, flash memory (e.g., flash memory such as NAND, 3D NAND, NOR, 3D NOR), EEPROM, MRAM, magnetic storage, hard discs, optical discs, etc. In other embodiments, the volatile storage media may take the form of RAM, TRAM, ZRAM, etc. Combinations of the above are also included within the scope of machine-readable media. In this regard, machine-executable instructions comprise, for example, instructions and data which cause a general pur- pose computer, special purpose computer, or special purpose processing machines to perform a certain function or group of functions. Each respective memory device may be oper- able to maintain or otherwise store data relating to the operations performed by one or more associated circuits, including processor instructions and related data (e.g., data- base components, object code components, script compo- nents), in accordance with the example embodiments described herein.

It should also be noted that the term "input devices," as described herein, may include any type of input device including, but not limited to, a keyboard, a keypad, a mouse, joystick or other input devices performing a similar func- tion. Comparatively, the term "output device," as described herein, may include any type of output device including, but not limited to, a computer monitor, printer, facsimile machine, or other output devices performing a similar func- tion.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated. Other substitutions, modifications, changes and omissions may be made in the design, operating conditions and embodiment of the embodiments without departing from the scope of the present disclosure as expressed in the appended claims.

What is claimed is:

1. A computer-implemented method for generating and managing one or more tasks associated with a medical device, the method comprising:

controlling, by a user interface circuit of a medical device task generation and management system, a front-end of a workflow management application comprising displaying a user interactive interface and receiving user interactions from the user interactive interface;

launching, by the user interface circuit on the front-end of the workflow management application, a Radio Frequency Identification (RFID) reader to read an RFID tag or a Near Field Communications (NFC) chip of the medical device;

controlling, by a patient management circuit and an analytics generation circuit of the medical device task generation and management system, a back-end of the workflow management application comprising handling and generating the one or more tasks and generating and providing one or more statistics or analytics;

determining, by the patient management circuit on the back-end of the workflow management application via the RFID tag or the NFC chip, device data identifying the medical device;

in response to receiving the device data, automatically generating, by the patient management circuit, the one or more tasks based on the device data on the workflow management application, each of the one or more tasks including a due date, a due time, and task data;

authenticating, by the patient management circuit, a staff computing device to access the workflow management application based on a one-time code transmitted via the user interface circuit, the staff computing device associated with a staff member assigned to the one or more tasks;

generating, by the user interface circuit on the user interactive interface of the front-end of the workflow management application, a device representation based on the device data, the device representation visually representative of the medical device;

providing, by the user interface circuit on the user interactive interface, an indicator for each of the one or more tasks within the device representation, the indicator providing a real-time visual indication within the device representation of a completion status of each of the one or more tasks based on the due date and the due time, the indicator comprising at least one of a first color associated with a corresponding task being overdue, a second color associated with the corresponding task being due, or a third color associated with the corresponding task not being due;

determining, by the patient management circuit, that at least one of the one or more tasks has been completed;

preventing, by the analytics generation circuit, the user interface circuit and the patient management circuit from performing any calculation-intensive data processing;

generating, by the analytics generation circuit, the one or more statistics or analytics associated with a plurality of medical devices comprising the medical device, the one or more statistics or analytics comprising a first quantity of the medical devices utilized within a first time period;

predicting, by the analytics generation circuit, a predicted quantity of the medical devices to be utilized within a second time period after the first time period; and in response to the predicted quantity being greater than a second quantity of the medical devices available in inventory, generating, by the analytics generation circuit, a purchase request for at least an additional quantity of the medical devices, the additional quantity being equal to a difference between the predicted quantity and the second quantity.

2. The method of claim 1, wherein the device data is received using the RFID reader and at least one of a quick response (QR) code scanner or a barcode scanner.

3. The method of claim 1, further comprising storing, by the patient management circuit, the task data associated with the at least one of the one or more tasks that has been completed in a server database.

4. The method of claim 1, further comprising receiving, by the patient management circuit, patient data associated with a patient, wherein the patient data comprises at least one of a room number of the patient, a name of the patient, or a date of birth of the patient.

5. The method of claim 1, wherein providing the indicator further comprises:

displaying, by the staff computing device, the user interactive interface including a patient representation;

generating and disposing, by the staff computing device, a device representation based on the device data on the user interactive interface; and updating, by the staff computing device based on the due date and the due time, a color of the device representation between at least one of the first color, the second color, or the third color.

6. The method of claim 1, further comprising:

receiving, by the patient management circuit, a request to update an electronic medical record of a patient; and providing, by the patient management circuit, at least one of patient data, the task data, or the device data to a third party electronic health record application.

7. The method of claim 6, wherein the at least one of the patient data, the task data, or the device data is provided via an application programming interface of the third party electronic health record application.

8. The method of claim 1, wherein determining that the at least one of the one or more tasks has been completed comprises receiving, by the patient management circuit, an indication that the at least one of the one or more tasks has been completed from the staff computing device.

9. The method of claim 1, wherein:

the medical device is a first medical device;

the device data is first device data;

the at least one of the one or more tasks comprises replacement of the first medical device; and determining that the at least one of the one or more tasks has been completed comprises receiving, by the patient management circuit, second device data associated with a second medical device that is a replacement of the first medical device, the second medical device and the first medical device being the same device type.

10. The method of claim 1, wherein generating the one or more tasks comprises:

providing, by the staff computing device, the task data associated with the medical device to at least one of a server computing device of the medical device task generation and management system or a health care provider computing device of the medical device task generation and management system;

searching, by the at least one of the server computing device or the health care provider computing device, a device database for the one or more tasks associated with the device data; and in response to the device database having the one or more tasks associated with the device data, providing, by the at least one of the server computing device or the health care provider computing device, the one or more tasks associated with the device data to the staff computing device.

11. The method of claim 1, further comprising:

in response to generating the one or more tasks, generating, by the patient management circuit, a reminder associated with at least one task of the one or more tasks and an alert associated with the at least one task, the reminder associated with a reminder time corresponding to time before or equal to the due time associated with the at least one task, the alert associated with an alert time corresponding to time after the due time associated with the at least one task; and in response to the reminder time being met, causing, by the user interface circuit, the reminder to be displayed on the staff computing device, the reminder not being displayed on a management computing device, the management computing device associated with a management member not assigned to the one or more tasks, wherein the one or more tasks is visible to the management computing device via the workflow management application.

12. The method of claim 11, further comprising:

in response to the alert time being met, causing, by the user interface circuit, the alert to be displayed on the staff computing device and the management computing device.

13. The method of claim 1, further comprising, prior to authenticating the staff computing device to access the workflow management application, providing, by the patient management circuit, an overview of the one or more tasks to the staff computing device.

14. A medical device task generation and management system, the system comprising:

a staff computing device comprising a network interface and a plurality of processing circuits, the network interface structured to facilitate data communication with a server computing device via a network, each of the processing circuits comprising a processor and a memory, the processing circuits structured to:

control, by a user interface circuit of the processing circuits, a front-end of a workflow management application comprising displaying a user interactive interface and receiving user interactions from the user interactive interface;

launch, by the user interface circuit on the front-end of the workflow management application, a Radio Frequency Identification (RFID) reader to read an RFID tag or a Near Field Communications (NFC) chip of a medical device;

control, by a patient management circuit and an analytics generation circuit of the processing circuits, a back-end of the workflow management application comprising handling and generating one or more tasks and generating and providing one or more statistics or analytics;

determine, by the patient management circuit on the back-end of the workflow management application via the RFID tag or the NFC chip, device data identifying the medical device;

in response to receiving the device data, automatically identify, by the patient management circuit, the one or more tasks based on the device data on the workflow management application, wherein each of the one or more tasks includes a due date, a due time, and task data;

authenticate, by the patient management circuit, the staff computing device to access the workflow management application based on a one-time code transmitted via the user interface circuit, the staff computing device associated with a staff member assigned to the one or more tasks;

generate, by the user interface circuit on the user interactive interface of the front-end of the workflow management application, a device representation based on the device data, the device representation visually representative of the medical device;

provide, by the user interface circuit on the user interactive interface, one or more indicators associated with each of the one or more tasks within the device representation to a user of the staff computing device, the one or more indicators providing a real-time visual indication within the device representation of a completion status of each of the one or more tasks based on the due date and the due time, the indicator comprising at least one of a first color associated with a corresponding task being overdue, a second color associated with the corresponding task being due, or a third color associated with the corresponding task not being due;

determine, by the patient management circuit, that at least one of the one or more tasks has been completed;

prevent, by the analytics generation circuit, the user interface circuit and the patient management circuit from performing any calculation-intensive data processing;

generate, by the analytics generation circuit, the one or more statistics or analytics associated with a plurality of medical devices comprising the medical device, the one or more statistics or analytics comprising a first quantity of the medical devices utilized within a first time period;

predict, by the analytics generation circuit, a predicted quantity of the medical devices to be utilized within a second time period after the first time period; and in response to the predicted quantity being greater than a second quantity of the medical devices available in inventory, generate, by the analytics generation circuit, a purchase request for at least an additional quantity of the medical devices, the additional quantity being equal to a difference between the predicted quantity and the second quantity.

15. The medical device task generation and management system of claim 14, wherein the device data is received from the RFID reader and at least one of a barcode scanner or a quick response (QR) code scanner of the staff computing device.

16. The medical device task generation and management system of claim 14, wherein the patient management circuit is further structured to provide, via the network interface, the task data associated with the at least one of the one or more tasks that has been completed to the server computing device.

17. The medical device task generation and management system of claim 14, wherein the patient management circuit is further structured to receive patient data associated with a patient, wherein the patient data comprises at least one of a room number of the patient, a name of the patient, or a date of birth of the patient.

18. The medical device task generation and management system of claim 14, wherein the user interface circuit is further structured to:

provide a patient representation on the user interactive interface;

generate and dispose a device representation based on the device data on the user interactive interface; and update, based on the due date and the due time, a color of the device representation between at least one of the first color, the second color, or the third color.

19. The medical device task generation and management system of claim 14, wherein the analytics generation circuit is further structured to:

receive a request to generate a custom report, the request including one or more data inputs specifying report data to be included within the custom report and a requesting party address;

generate the custom report based on the one or more data inputs; and provide the custom report to the requesting party address.

20. The medical device task generation and management system of claim 19, wherein the request to generate the custom report is received from the user interactive interface generated and displayed by the staff computing device, the user interactive interface including at least one of a drop down box or a plurality of check boxes through which the user can select the one or more data inputs of the request.

21. A non-transitory computer readable medium having computer-executable instructions embodied therein that, when executed by a plurality of processing circuits of a computing system, cause the computing system to perform operations to generate and manage one or more tasks associated with a medical device, the operations comprising:

control, by a user interface circuit of the processing circuits, a front-end of a workflow management application comprising displaying a user interactive interface and receiving user interactions from the user interactive interface;

launch, by the user interface circuit on the front-end of the workflow management application, a Radio Frequency Identification (RFID) reader to read an RFID tag or a Near Field Communications (NFC) chip of the medical device;

control, by a patient management circuit and an analytics generation circuit of the processing circuits, a back-end of the workflow management application comprising handling and generating the one or more tasks and generating and providing one or more statistics or analytics;

determine, by a patient management circuit on the back-end of the workflow management application via the RFID tag or the NFC chip, device data identifying the medical device;

in response to receiving the device data, automatically generate, by the patient management circuit, the one or more tasks based on the device data on the workflow management application, each of the one or more tasks including a due date, a due time, and task data;

authenticate, by the patient management circuit, a staff computing device to access the workflow management application based on a one-time code transmitted via the user interface circuit, the staff computing device associated with a staff member assigned to the one or more tasks;

generate, by the user interface circuit on the user interactive interface of the front-end of the workflow management application, a device representation based on the device data, the device representation visually representative of the medical device;

generate and provide, by the user interface circuit on the user interactive interface, one or more indicators based on each of the one or more tasks within the device representation to a user of a computing device, the one or more indicators providing a real-time visual indication within the device representation of a completion status of each of the one or more tasks based on the due date and the due time, the indicator comprising at least one of a first color associated with a corresponding task being overdue, a second color associated with the corresponding task being due, or a third color associated with the corresponding task not being due;

determine, by the patient management circuit, that at least one of the one or more tasks has been completed;

prevent, by the analytics generation circuit, the user interface circuit and the patient management circuit from performing any calculation-intensive data processing;

generate, by the analytics generation circuit, the one or more statistics or analytics associated with a plurality of medical devices comprising the medical device, the one or more statistics or analytics comprising a first quantity of the medical devices utilized within a first time period;

predict, by the analytics generation circuit, a predicted quantity of the medical devices to be utilized within a second time period after the first time period; and in response to the predicted quantity being greater than a second quantity of the medical devices available in inventory, generate, by the analytics generation circuit, a purchase request for at least an additional quantity of the medical devices, the additional quantity being equal to a difference between the predicted quantity and the second quantity.

22. The non-transitory computer readable medium of claim 21, wherein the operations further comprise receiving, by the patient management circuit, patient data associated with a patient, wherein the patient data comprises at least one of a room number of the patient, a name of the patient, or a date of birth of the patient.

23. The non-transitory computer readable medium of claim 21, wherein:

the medical device is a first disposable medical device;

the device data is first device data;

the at least one of the one or more tasks comprises replacement of the first disposable medical device; and the operations further comprise:

receive, by the patient management circuit, second device data associated with a second disposable medical device that is a replacement of the first disposable medical device, the first disposable medical device and the second disposable medical device being the same device type, and determine, by the patient management circuit based on the first disposable medical device and the second disposable medical device being the same device type, that the at least one of the one or more tasks has been completed.

\* \* \* \* \*